(12) United States Patent
Desmond et al.

(10) Patent No.: US 8,623,296 B2
(45) Date of Patent: Jan. 7, 2014

(54) MICROFLUIDIC SIZE-EXCLUSION DEVICES, SYSTEMS, AND METHODS

(75) Inventors: Sean M. Desmond, San Carlos, CA (US); Zbigniew T. Bryning, Campbell, CA (US); John Shigeura, Portola Valley, CA (US); Gary Lim, San Francisco, CA (US); Adrian Fawcett, Pleasanton, CA (US); Jacob K. Freudenthal, San Jose, CA (US); Gary Bordenkircher, Livermore, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/850,326

(22) Filed: Aug. 4, 2010

(65) Prior Publication Data

US 2010/0298172 A1 Nov. 25, 2010

Related U.S. Application Data

(60) Continuation of application No. 11/796,783, filed on Apr. 30, 2007, now abandoned, which is a division of application No. 10/336,706, filed on Jan. 3, 2003, now Pat. No. 7,214,348.

(60) Provisional application No. 60/398,851, filed on Jul. 26, 2002, provisional application No. 60/398,946, filed on Jul. 26, 2002, provisional application No. 60/399,548, filed on Jul. 30, 2002.

(51) Int. Cl.
*C12M 1/00* (2006.01)
*C40B 60/00* (2006.01)

(52) U.S. Cl.
USPC ............ 422/506; 422/50; 422/68.1; 422/70; 422/72; 422/129; 422/131; 422/503; 422/504; 422/507; 422/513; 422/527; 422/534; 422/535; 435/161; 435/283.1; 435/285.1; 435/286.2; 435/287.2; 435/287.3; 435/288.4; 435/288.6; 435/288.7; 435/289.1; 436/94; 436/106; 436/111; 436/161; 436/164; 506/33

(58) Field of Classification Search
USPC .......... 422/50, 62–64, 68.1, 70, 72, 129, 134, 422/136, 139–141, 500–504, 506, 513, 527, 422/534, 535
See application file for complete search history.

(56) References Cited

U.S. PATENT DOCUMENTS 3,990,858 A 11/1976 O'Sullivan et al. ............. 23/288
4,787,988 A 11/1988 Bertoncini et al.
(Continued)

FOREIGN PATENT DOCUMENTS

DE 199 35 433 A1 3/2001
JP 2-149321 6/1990
(Continued)

OTHER PUBLICATIONS

International Search Report, mailed Jan. 9, 2004, for International Application No. PCT/US03/22773.
(Continued)

*Primary Examiner* — Jill Warden
*Assistant Examiner* — Timothy G Kingan

(57) ABSTRACT

Microfluidic devices, assemblies, and systems are provided, as are methods of manipulating micro-sized samples of fluids. Microfluidic devices having a plurality of specialized processing features are also provided.

5 Claims, 13 Drawing Sheets

(56) References Cited

U.S. PATENT DOCUMENTS

| | | | |
|---|---|---|---|
| 4,948,564 A | 8/1990 | Root et al. | |
| 5,061,381 A | 10/1991 | Burd | 210/789 |
| 5,081,017 A | 1/1992 | Longoria | |
| 5,085,058 A | 2/1992 | Aaron et al. | 62/324.6 |
| 5,154,888 A | 10/1992 | Zander et al. | |
| 5,173,262 A | 12/1992 | Burtis et al. | 422/72 |
| 5,242,606 A | 9/1993 | Braynin et al. | 210/787 |
| 5,242,803 A | 9/1993 | Burtis et al. | 435/7.92 |
| 5,296,375 A | 3/1994 | Kricka et al. | 435/291 |
| 5,304,487 A | 4/1994 | Wilding et al. | 435/291 |
| 5,484,572 A | 1/1996 | Katakura et al. | |
| 5,498,392 A | 3/1996 | Wilding et al. | 422/68.1 |
| 5,591,643 A | 1/1997 | Schembri | 436/45 |
| 5,635,358 A | 6/1997 | Wilding et al. | 435/7.2 |
| 5,726,026 A | 3/1998 | Wilding et al. | 435/7.21 |
| 5,744,366 A | 4/1998 | Kricka et al. | 436/63 |
| 5,792,425 A | 8/1998 | Clark et al. | |
| 5,928,880 A | 7/1999 | Wilding et al. | 435/7.21 |
| 6,063,282 A | 5/2000 | Moulton | |
| 6,143,248 A | 11/2000 | Kellogg et al. | 422/72 |
| 6,184,029 B1 | 2/2001 | Wilding et al. | 435/287.1 |
| 6,193,647 B1 | 2/2001 | Beebe et al. | 600/33 |
| 6,296,020 B1 | 10/2001 | McNeely et al. | 137/806 |
| 6,402,950 B1 | 6/2002 | Nix et al. | |
| 6,426,230 B1 | 7/2002 | Feistel | |
| 6,457,236 B1 | 10/2002 | White et al. | 29/890.08 |
| 6,479,299 B1 | 11/2002 | Parce et al. | 436/514 |
| 6,503,457 B1 | 1/2003 | Neeper et al. | |
| 6,609,618 B2 | 8/2003 | Colpan | |
| 6,627,159 B1 | 9/2003 | Bedingham et al. | |
| 7,041,258 B2 | 5/2006 | Desmond et al. | |
| 7,198,759 B2 | 4/2007 | Bryning et al. | |
| 7,214,348 B2 | 5/2007 | Desmond et al. | |
| 2002/0047003 A1* | 4/2002 | Bedingham et al. | 219/388 |
| 2002/0048533 A1 | 4/2002 | Harms et al. | |
| 2002/0064885 A1 | 5/2002 | Bedingham et al. | |
| 2002/0074227 A1 | 6/2002 | Nisch et al. | 204/450 |
| 2002/0076354 A1 | 6/2002 | Cohen | 422/72 |
| 2002/0150512 A1 | 10/2002 | Kellogg et al. | 422/103 |

FOREIGN PATENT DOCUMENTS

| | | |
|---|---|---|
| JP | 7-103971 | 4/1995 |
| WO | WO 01/08799 A1 | 2/2001 |
| WO | WO 01/25138 A1 | 4/2001 |
| WO | WO 02/074438 A2 | 9/2002 |

OTHER PUBLICATIONS

Supplemental Partial European Search Report mailed Jun. 28, 2005.

* cited by examiner

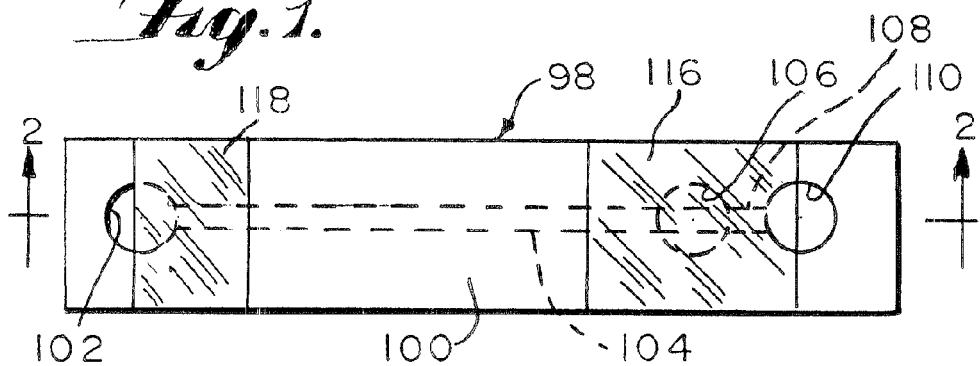
Fig. 1.
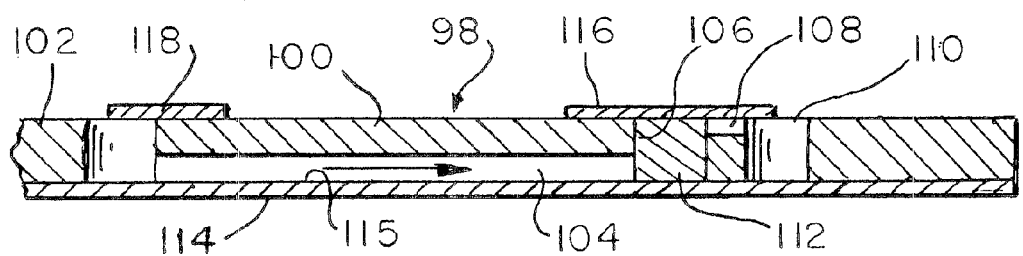
Fig. 2.
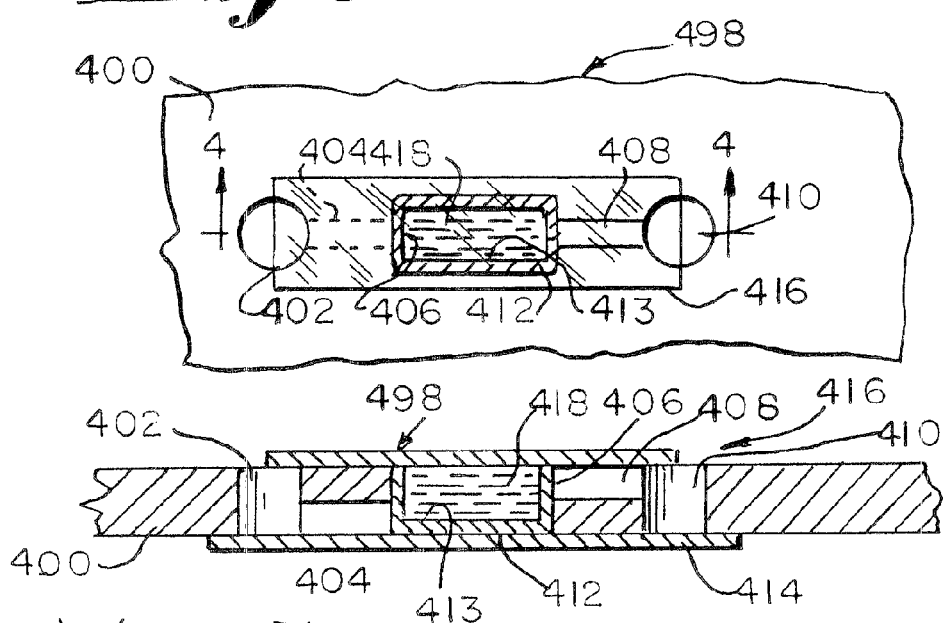
Fig. 3.
Fig. 4.

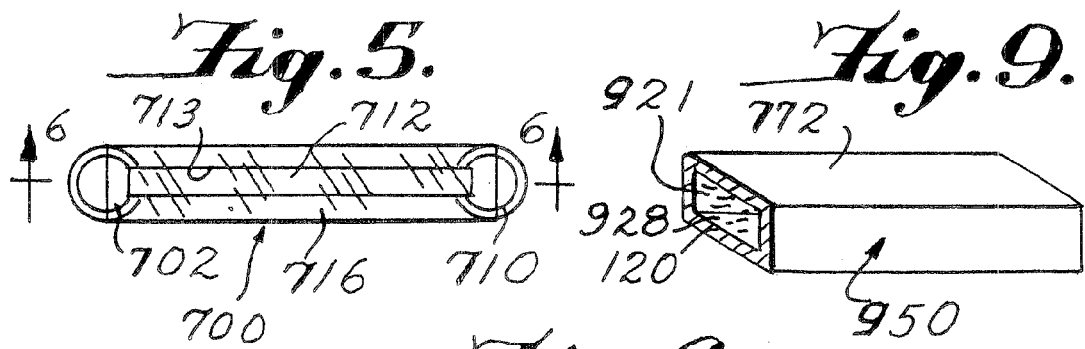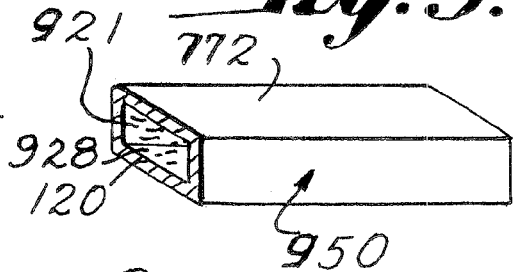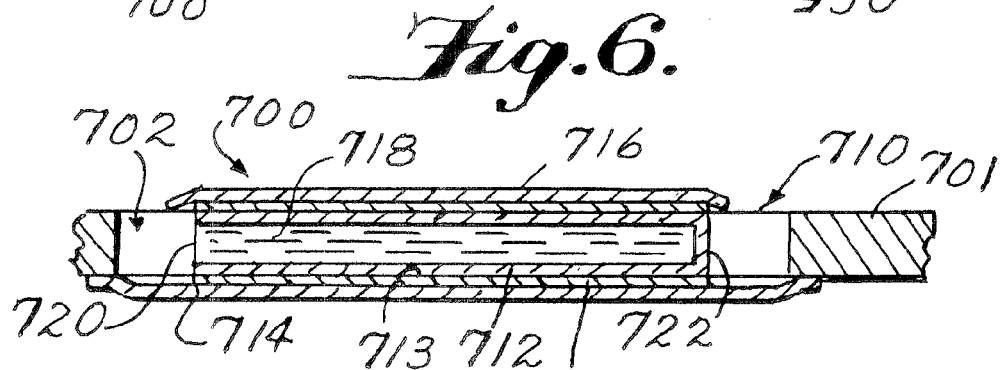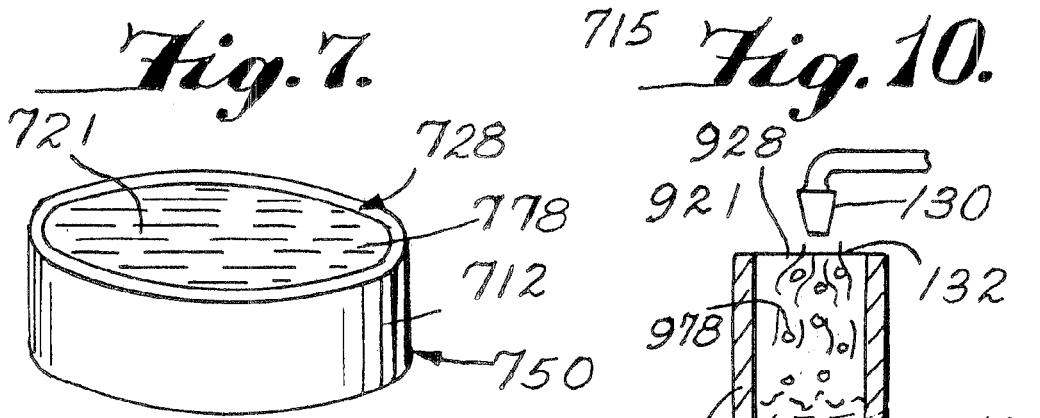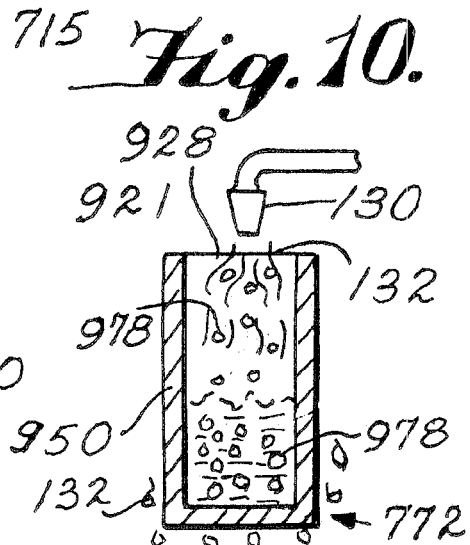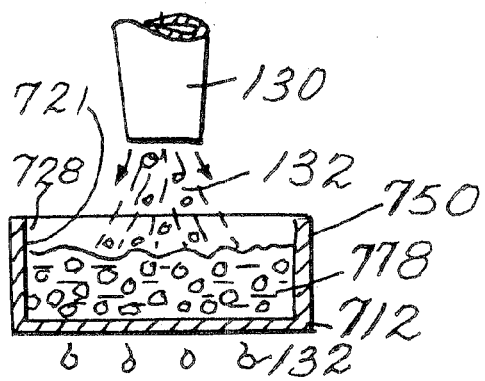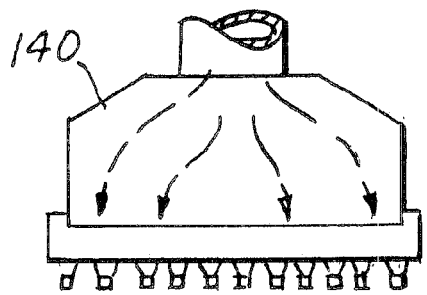

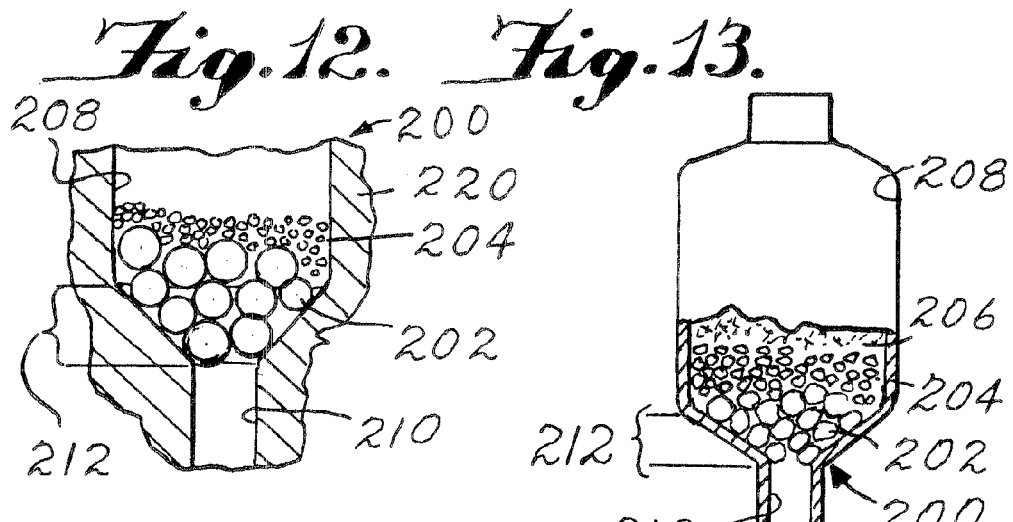
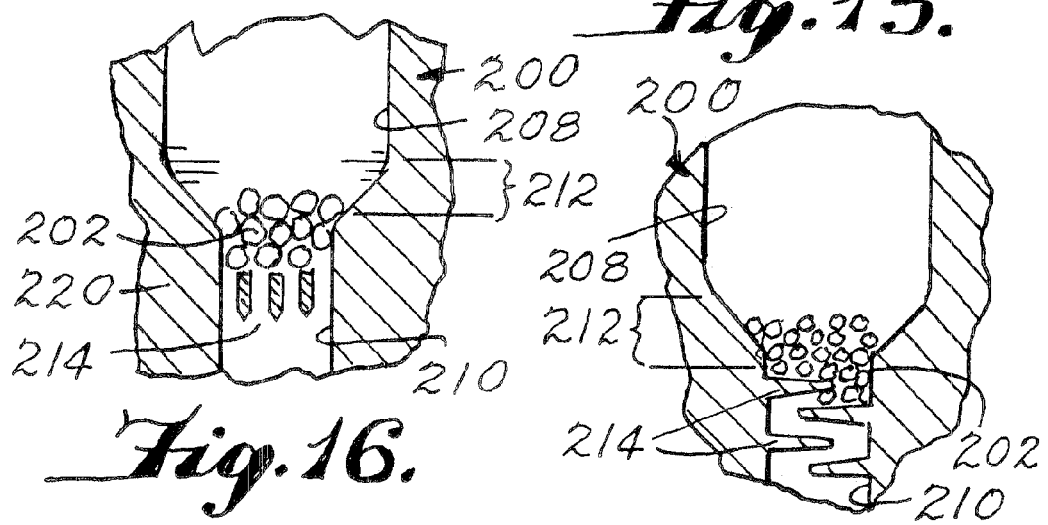
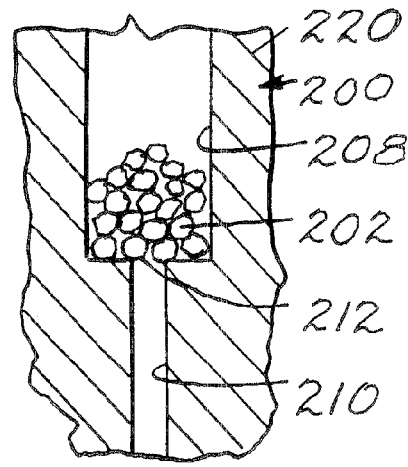
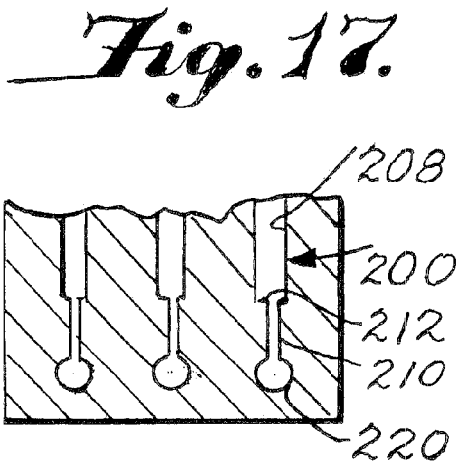

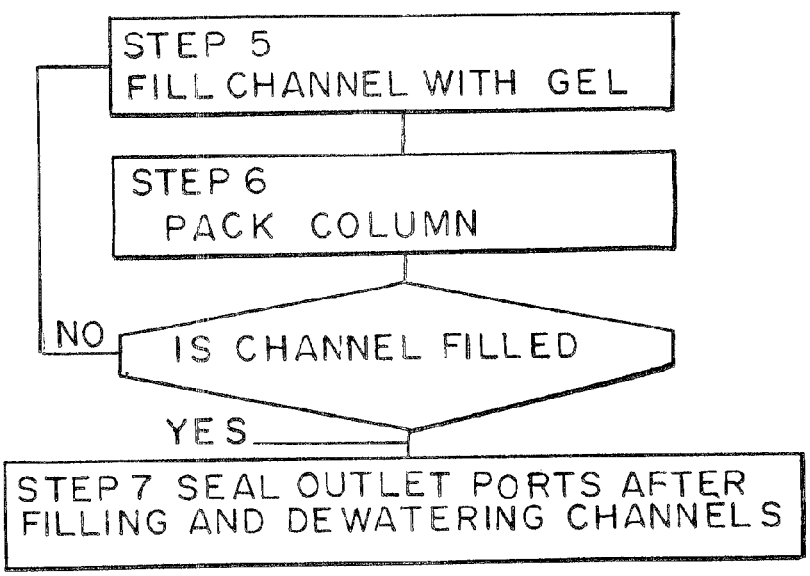

MICROFLUIDIC SIZE-EXCLUSION DEVICES, SYSTEMS, AND METHODS

CROSS REFERENCE TO RELATED APPLICATIONS

The present application is a Continuation Application of U.S. patent application Ser. No. 11/796,783 filed Apr. 30, 2007 now abandoned, which is a Divisional Patent Application of U.S. patent application Ser. No. 10/336,706 filed Jan. 3, 2003, now U.S. Pat. No. 7,214,348, which issued on May 8, 2007, which claims benefit under 35 U.S.C. §119(e) from earlier filed U.S. Provisional Patent Application Nos. 60/398,851 and 60/398,946, both filed Jul. 26, 2002, and U.S. Provisional Patent Application No. 60/399,548, filed Jul. 30, 2002; all of which are herein incorporated in their entireties by reference. Cross-Reference is also hereby made to U.S. patent application Ser. Nos. 10/336,274, now U.S. Pat. Nos. 7,198,759, and Ser. No. 10/336,330, now U.S. Pat. No. 7,041,258, both filed Jan. 3, 2003, both of which are also herein incorporated in their entireties by reference.

FIELD

The present application relates to microfluidic devices, systems that include such devices, and methods that use such devices and systems. More particularly the present invention relates to devices that manipulate, process, or otherwise alter micro-sized amounts of fluids and fluid samples.

BACKGROUND

Microfluidic devices are useful for manipulating fluid samples. There continues to exist a demand for microfluidic devices, systems of using them, systems for processing them, and methods of manipulating fluids, that are fast, reliable, consumable, and can be used to process a large number of samples simultaneously.

SUMMARY

According to various embodiments, a microfluidic device is provided that includes a substrate, a first channel, a second channel, a column connecting the first and second channels, and a filter frit material disposed in the column. The substrate can have first and second opposing surfaces and a thickness. The first channel can be formed in the first surface and can have a first depth extending in a direction normal to the first surface and toward the second surface. The first depth can be equal to or less than the thickness of the substrate. The second channel can be formed in the second surface and can have a second depth extending in a direction normal to the second surface and toward the first surface. The second depth can be equal to or less than the thickness of the substrate. The column can have a height that extends from the first surface to the second surface. The column can have a constant cross-sectional area and/or a constant diameter, along planes that lie parallel to the first surface, from the first surface to the second surface.

According to various embodiments, an integrated gel filtration frit is provided that includes a body comprising a form-stable filter fit material, a chamber formed in the body, and a gel filtration material disposed in the chamber.

According to various embodiments, a microfluidic device is provided that includes a substrate, a first channel, a second channel, a fluid communication between the first channel and the second channel, and a flow-restricting particulate material piled-up or log-jammed at the fluid communication. According to such embodiments, the substrate can have a first surface, a second surface opposing the first surface, and a thickness. The first channel can be formed in the substrate and can extend in a first direction. The first channel can have a first cross-sectional area defined by at least a first minimum dimension and a first depth, the first depth extending in a direction normal to the first surface and toward the second surface. The second channel can be formed in the substrate and can extend in a second direction. The second channel can have a second cross-sectional area defined by at least a second minimum dimension and a second depth, the second depth extending in a direction normal to the first surface and toward the second surface. The fluid communication can be formed in the substrate between the first channel and the second channel and can have a third cross-sectional area defined by at least a third minimum dimension, where the third cross-sectional area is less than the first cross-sectional area. The flow-restricting material can be disposed in the first channel, in the fluid communication, or in both the first channel and in the fluid communication. The flow-restricting material can include gel filtration particles, where at least 10% by weight of the flow-restricting particles comprises flow-restricting particles having an average particle diameter that is less than the third minimum dimension.

According to various embodiments, a microfluidic device is provided that includes a substrate, a first channel formed in the substrate, and a first chamber formed in the substrate, wherein the first chamber has a depth and a teardrop-shaped cross-sectional area when cross-sectioned perpendicular to the depth. The first chamber can have a substantially circular first end and a narrower and opposite second end, which ends collectively define a teardrop-shaped cross-section. The cross-section of the first chamber can be constant along the depth of the first chamber. The second end of the first chamber can be in fluid communication with the first channel.

According to various embodiments, a microfluidic device is provided that includes a substrate having a first surface, a second surface opposing the first surface, and a thickness, and a plurality of parallel pathways formed in the substrate, wherein each of the pathways comprises an input opening, an output opening, at least one processing chamber located between the input opening and the output opening, and wherein the input opening, the at least one processing chamber, and the output opening at each pathway are arranged linearly. Each of the plurality of parallel pathways can include at least one valve that is capable of being actuated to provide a fluid communication between the at least one processing chamber and at least one of the input opening and the output opening. Each of the plurality of pathways can include at least one valve that comprises a first deformable material having a first elasticity, a second deformable material having a second elasticity that differs from the first elasticity, and an adhesive material.

According to various embodiments, a sample processing system is provided that includes a microfluidic device as described herein, a platen, a drive unit, and a control unit wherein the platen includes a microfluidic device holder to hold the microfluidic device. The microfluidic device can have a substrate having a first surface, a second surface opposing the first surface, and a thickness, and a plurality of parallel pathways formed in the substrate, each of the pathways comprising an input opening, an output opening, and at least one processing chamber between and in fluid communication with the input opening and the output opening. The platen can have an axis of rotation and the holder can be disposed spaced from, and off-center with respect to, the axis of rotation. The drive unit can be capable of rotating the platen about the axis of rotation, and the control unit can be capable of controlling the drive unit.

According to various embodiments, a method of fabricating a microfluidic device is provided, wherein the microfluidic device includes a substrate, an input opening formed in the substrate, a first channel formed in the substrate and in fluid communication with the input opening, a second channel formed in the substrate, and a fluid communication between the first channel and the second channel. The method can include introducing a flow-restricting material through the input opening and into the first channel, and applying centripetal force to the microfluidic device to pack the flow-restricting material in the first channel at the fluid communication and to prevent a substantial portion of the flow-restricting material from moving through the fluid communication and into the second channel.

According to various embodiments, a microfluidic device is provided having a substrate, a first recess formed in the substrate, a second recess formed in the substrate, and an intermediate wall interposed between the first recess and the second recess, wherein the intermediate wall portion is formed from a deformable material having a first elasticity. An elastically deformable cover layer is also provided covering the first recess, and a particulate flow-restricting material can be disposed in the first recess. The elastically deformable cover layer can have a second elasticity that is less than the first elasticity, wherein the elastically deformable covered layer contacts the intermediate wall when the intermediate wall is in a non-deformed state, and wherein the elastically deformable cover layer does not contact the intermediate wall when the intermediate wall is in a deformed state, thereby forming a fluid communication between the first and second recesses. The fluid communication between the first and second recesses can be designed or formed as a flow restrictor as described herein.

The invention may be more fully understood with reference to the accompanying drawing figures and the descriptions thereof. Modifications that would be recognized by those skilled in the art are considered a part of the present disclosure and within the scope of the appended claims.

BRIEF DESCRIPTION OF THE DRAWINGS

FIG. 1 is a top view of a microfluidic device according to an embodiment wherein a first channel is formed in a first surface, a second channel is formed in a second surface, and an interconnecting column of constant diameter and having a frit material disposed therein;

FIG. 2 is a cross-sectional side view of the microfluidic device shown in FIG. 1 taken along line 2-2 of FIG. 1;

FIG. 3 is a top view of another embodiment of a microfluidic device including an integrated gel filtration frit;

FIG. 4 is a cross-sectional side view of the microfluidic device shown in FIG. 3 taken along line 4-4 of FIG. 3;

FIG. 5 is a top view of a microfluidic device according to an embodiment including an integrated gel filtration frit;

FIG. 6 is a cross-sectional side view of the microfluidic device shown in FIG. 5 taken along line 6-6 of FIG. 5;

FIG. 7 is a perspective view of an integrated gel filtration frit having a form-stable body, a chamber in the body, and a gel filtration material disposed in the chamber;

FIG. 8 is a cross-sectional side view of an integrated gel filtration frit including a form-stable body as shown in FIG. 7 being filled with a gel filtration material by using a nozzle;

FIG. 9 is a perspective view of a form-stable body for use in preparing an integrated gel filtration frit and having a chamber;

FIG. 10 is a cross-sectional side view of the form-stable body shown in FIG. 9 being filled with a gel filtration material by using a nozzle;

FIG. 11 is a perspective view of a multi-nozzle machine useful in filling a plurality of integrated gel filtration fits simultaneously;

FIG. 12 is a top view in partial cross-section of a microfluidic device that includes a fluid communication having a conical shape, and including two types of particles sizes;

FIG. 13 is a top view in partial cross-section of an embodiment of a side view of a microfluidic device including a gel filtration material that can be used as a flow restrictor;

FIGS. 14 and 15 are top views in partial cross-section of embodiments of a microfluidic device having baffles to restrict the flow of fluid and cause a pile-up of gel filtration particles;

FIGS. 16 and 17 are top views of various embodiment of a microfluidic device including a fluid communication having an abrupt change in the cross-sectional area between a first channel and a second channel;

FIG. 18 is a flowchart with corresponding cross-sectional views, depicting a method for forming a microfluidic device;

FIG. 19 is a flowchart depicting a method of preparing a microfluidic device for use as a purification device;

Figure 20:
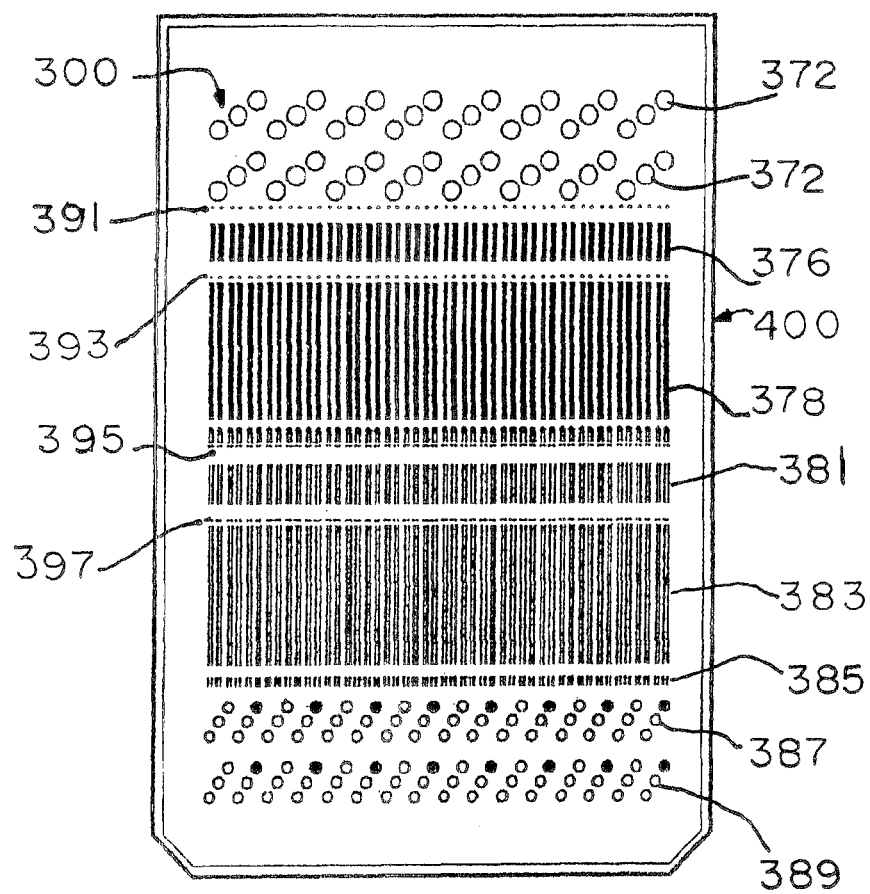
FIG. 20 is a top view of an embodiment of a microfluidic device having a substrate, a plurality of parallel pathways formed in the substrate, and a plurality of valves for each pathway.

Other various embodiments of the present invention will be apparent to those skilled in the art from consideration of the specification and practice of the devices, systems, and methods described herein, and the detailed description that follows. It is intended that the specification and examples be considered as exemplary only, and that the true scope and spirit of the invention includes those other various embodiments.

DETAILED DESCRIPTION OF CERTAIN EMBODIMENTS

FIG. 1 is a top view of a microfluidic device 98 according to various embodiments that include a substrate 100, an input opening 102, an output opening 110, a first channel 104, a second channel 108, a chamber 106 interconnecting the first channel 104 and the second channel 108, and a filter frit material 112 disposed in the chamber 106. The chamber 106 can be in the form of a column, for example, a vertical cylindrical column as shown.

FIG. 2 is a cross-sectional side view of the microfluidic device 98 of FIG. 1, taken along line 2-2 of FIG. 1. As shown in FIGS. 1 and 2, covers 114, 116, and 118 are provided in contact with the substrate 100. Cover 114 covers the bottom, as shown in FIG. 2, of the substrate 100 and provides an inner surface 115 that can, in-part, define channel 104. A fluid sample introduced in input opening 102 can pass from input opening 102 into first channel 104, through first channel 104 and into chamber 106, through filter fit material 112 in chamber 106 and into second channel 108, and from second channel 108 into output opening 110. First channel 104 can be loaded with a gel filtration material (not shown), for example, an ion-exchange gel filtration material.

Input opening 102 can be designed as an entry port, a hole through a layer, an aperture, or any other feature that provides an entrance to a channel or chamber in fluid communication therewith. Output opening 110 can be designed as a port, aperture, a hole through a layer, or any other feature that provides an exit from a channel or chamber in fluid communication therewith. Input opening 102 and/or output opening 110 can be covered or partially covered by a frangible or puncturable material cover 116,118 that can be in the form of a tape, a film, a sheet, a membrane, or a combination thereof. Cover 114 for the bottom (as shown) of the device can be a tape, a film, a sheet, a membrane, or a combination thereof. Any of covers 114, 116, and 118 can be in the form of a second substrate affixed to, secured to, bonded to, or otherwise connected to the substrate 100. First channel 104, second channel 108, chamber 106, or combinations thereof can be pre-filled with reagents, reactants, or buffers known in the art, before the respective cover is applied to substrate 100. Additionally, first channel 104, second channel 108, chamber 106, or combinations thereof can be loaded through the input opening.

FIG. 3 is a top view of a microfluidic device 498 that includes a filter frit material 412 having a shape that complements the shape of a column 406 in which the filter frit material 412 is disposed. The filter frit material 412 can include a chamber 413 that retains a gel filtration material 418. FIG. 4 is a side view of the microfluidic device 498 shown in FIG. 3. In the embodiment shown in FIGS. 3 and 4, the device further includes a substrate 400, an input opening 402, a first channel 404, a chamber 406 for accommodating filter frit material 412, a second channel 408, and an output opening 410. The device 498 shown in FIGS. 3 and 4 can also include a first cover 414, and a second cover 416. The filter frit material 412 can have an outer shape that is complementary to the inner shape of chamber 406.

FIGS. 5 and 6 show an embodiment of a microfluidic device 700 that includes a substrate 701 and a filter frit material 712 having a shape that complements a chamber 713. An opening 720 of the filter fit material 712 faces an input opening 702 formed in substrate 701. The filter frit material 712 further includes a closed end 722 oriented towards an output opening 710 formed in a substrate 701. The filter frit material 712 can be filled with a filtration material 718, for example, an ion-exchange gel filtration material. Covers 714 and 716 can be secured, bonded, adhered, or otherwise affixed to substrate 701 using an adhesive 715. The adhesive can be, for example, a pressure sensitive adhesive.

The microfluidic devices 98, 498, and 700 shown in FIGS. 1-6 can be used for filtering liquids that are manipulated to pass through the devices. The devices can be used, for example, for gel filtration, size-exclusion filtration, ion-exchange filtration, or combinations of these filtration techniques. For example, filtration materials can be loaded and/or included in the devices, and can include small beads of filtration materials. Size-exclusion materials can be used that can retain smaller molecules of an aqueous sample while allowing larger molecules of the sample to pass through or around. For example, P-10 BIO-GEL materials from Bio-Rad can be used and are composed of acrylamide particles that are roughly 45-90 µm in average particle size diameter. These particles, when hydrated, can capture free dyes, undesired nucleotides, and salt ions from a sample as the sample migrates through the materials.

Samples can be manipulated through devices 98, 498, and 700 by gravity pressure differentials, or centripetal force, for example. The resulting filtrates that elute from the devices can then be analyzed, used, or subsequently passed on through the device to a subsequent stage of processing, for example, into a PCR reaction chamber, a sequencing reaction chamber, or other processing reaction chamber.

According to various embodiments, the filter frit material 112, 412, or 712 shown in FIGS. 1-6 can be "press fit" into the respective chamber, placed in the respective chamber, or otherwise positioned in the respective chamber.

The covers described above with reference to FIGS. 1-6 can include a plastic material, for example, a polyolefin material. According to various embodiments, covers can include tape or film materials coated with a pressure-sensitive adhesive, or plastic materials that can be thermally bonded to a respective substrate.

According to various embodiments including those shown in FIGS. 1-6, the device can include one or more channels that can be rectangular in cross-sectional shape. The devices can include channels that can be, for example, from about 0.1 mm to about 1.0 cm deep, from about 0.1 mm to about 1.0 cm wide, and from about 0.1 mm to about 10.0 cm long. An exemplary channel can be 0.50 mm deep, 0.50 mm wide, and 20 mm long, thus providing total volume of about 5 µL.

According to various embodiments including those of FIGS. 1-6, a gel filtration material can be disposed in a channel of the device. The gel filtration material can be loaded into the device by pipetting into an input opening of the device and/or drawing the material into the device by using vacuum force, for example, applied to an output opening of the device. A channel of the device can be filled with a gel filtration material by pressure loading the gel filtration material through an input opening of the device to dispense the gel filtration material in a channel or chamber of the device. In an exemplary embodiment, a fully hydrated gel filtration material is loaded into a channel of the device, for example, into first channel 104 of device 98 of FIG. 1. Once the channel is filled with hydrated gel filtration material, the device can be centrifuged to de-water the gel filtration material and to "pack" the gel filtration material, forming a purification column. This process can be used to prepare the device for sample filtration and can be used to remove unnecessary or excess water or buffer from the gel filtration material. In a variant of this process, the excess water or buffer can be collected in an outlet channel or chamber and later used to dilute and increase the volume of a filtered sample to render the sample injection-ready.

According to various embodiments including the embodiments of FIGS. 1-6, the device can include additional chambers and/or channels. For example, the device can include a PCR amplification chamber, a sequencing reaction chamber, or both a PCR amplification chamber and a sequencing reaction chamber. According to various embodiments, the device can include an output chamber useful for holding a sample prior to injecting the sample into a sequence detection system or other analytical detector.

According to various embodiments, microfluidic devices are provided that include a plurality of sample processing pathways as described herein, in a single device.

According to various embodiments, a porous filter frit material can be used to prevent the gel filtration material loaded in a channel from flowing out of the channel. The average pore size of the filter frit material can be chosen to allow fluids to pass through (water, sample, etc.) while constraining the movement of a gel filtration material such as acrylamide beads. For instance, the microfluidic device shown in the FIGS. 1-6 can utilize a hydrophilic polyethylene filter frit material with an average pore size of about 33 microns. When used with P-10 BIO-GEL gel filtration materials, such a frit can adequately constrain the gel filtration materials while allowing water and sample fluids to pass therethrough. An exemplary porous filter frit material that can be used for such purpose is a sintered, high-density polyethylene (HDPE) frit having a suitable average pore size.

According to various embodiments, a gel filtration retention mechanism can be provided in a device and includes a flow-restrictor in the form of a small channel or serpentine path formed in the substrate and which prevents the gel filtration material from passing.

According to various embodiments including the embodiments of FIGS. 1-4, wherein two channels are provided and separated by a filtration chamber or column, one of the channels can be formed in a first surface of a substrate and a second channel can be formed in the opposing surface of the substrate. For example, the second channel 108 (FIG. 2) or 408 (FIG. 4) can be formed in a first surface of the substrate and can provide fluid communication between a processing chamber and a respective output opening.

The second channel can have dimensions similar to, or the same as, the dimensions of the first channel, as illustrated in FIGS. 3 and 4. The second channel can have a depth of from about 0.1 mm to about 1.0 cm, a width of from about 0.1 mm to about 1.0 cm, and a length of from about 0.1 mm to about 10.0 cm. An exemplary second channel has a depth of about 0.50 mm, a width of about 0.75 mm and a length of about 3.0 mm. The second channel can be at least partially defined by a cover, for example, cover 116 shown in FIGS. 1 and 2, or figure 416 shown in FIGS. 3 and 4. Regardless of whether the device includes a first channel filled with a gel filtration material, the second channel of the device can be provided with a gel filtration material loaded therein. Gel filtration material can be loaded into the second channel before, after, or at the same time that a filtration frit is positioned within the device.

According to various embodiments, the output opening 110, 410, 710 can serve to capture or retain a processed sample after the sample passes through a processing chamber in the microfluidic device. Initially, the output opening 110, 410, 710 can be open so that vacuum can be applied to the device for loading a gel filtration material. The output opening can remain open during centrifugation of the microfluidic device to further pack and/or dewater the gel filtration material. During such a packing process, excess water or buffer can be purged from the device and can escape the device through the outlet opening 110, 410, 710. When a sample is manipulated through the microfluidic device, as by centrifugation, for example, the outlet opening 110, 410, 710 can be sealed with a cover film 116, 416, 716 to prevent the sample from being lost, or to otherwise retain the sample in the device.

According to various embodiments, a microfluidic device can be provided with a plurality of pathways formed in a substrate, with each pathway being similar to one of the pathways shown in FIG. 1-6. Using channels and chambers having widths of about 0.50 mm or less, for example, it is possible to provide up to 96 or more such pathways in the substrate and to provide a resulting substrate size equivalent to that of a standard micro-titer tray, for example, a length of about 4.75 inches and a width of about 3.25 inches. An exemplary device of such design is shown in FIG. 20 and incorporates the 5 µL gel filtration columns.

According to various embodiments, a microfluidic device is provided similar to those shown in FIGS. 1-4 and having a substrate that includes a thickness that is greater than the sum of the depth of the first channel and the depth of the second channel. According to various embodiments, a microfluidic device is provided similar to the device shown in FIGS. 5 and 6 and having a substrate that includes a thickness that is the same as the depth of the filter chamber 713.

According to various embodiments, including the embodiments of FIGS. 1-6, a microfluidic device is provided wherein the filtration frit material 112, 412, 712 has an outer peripheral shape, the chamber 106, 406, 713 has an inner peripheral shape, and the outer peripheral shape is complementary to the inner peripheral shape.

FIGS. 7 and 9 depict exemplary embodiments of an integrated gel filtration frit 750, 950 that includes a body 712, 772 made up of a form-stable frit material and that defines a chamber 721, 921 and an opening 728, 928. The chamber 721, 921 is filled with a gel filtration material 778, 978 that has been loaded in the chamber 721, 921. The gel filtration frit 750, 950 can be made by a method as depicted in FIGS. 8 and 10, respectively.

FIGS. 8 and 10 illustrate a nozzle 130 in the process of filling the integrated gel filtration frits 750, 950 with a diluent 132 and a gel filtration material 778, 978 via the opening 728, 928.

FIG. 11 depicts an embodiment of a multi-nozzle filling machine 140 for simultaneously filling a plurality of integrated gel filtration frits.

According to various embodiments, an integrated gel filtration frit 750, 950 can be formed as illustrated in FIGS. 8 and 10 and subsequently packed into a microfluidic device, for example, a device as shown in FIGS. 3-6. For instance, a slurry of hydrated P-10 BIO-GEL particles can be pumped into a porous form-stable frit body, and the resulting frit can be assembled into a microfluidic device. Such a manufacturing procedure can reduce the number of substrate manipulations involved with forming the microfluidic device, allow for off-line filtration frit fabrication, and can reduce the overall manufacturing costs for the microfluidic device.

According to various embodiments, the body and/or chamber of the integrated gel filtration frit can be constructed in a rectanguloid or a cylindrical shape, and the chamber can be pre-filled with more than one type of gel using a single nozzle or multiple nozzles.

The integrated gel filtration frit can retain a gel filtration material therein yet allow water and liquid samples to flow therethrough.

According to various embodiments, an integrated gel filtration fit can be provided that includes an opening in a frit body which is in fluid communication with an interior gel filtration material chamber. According to various embodiments, an integrated gel filtration frit can be provided having a gel filtration material that includes an ion-exchange gel filtration material. According to various embodiments, an integrated gel filtration frit can be provided having a form-stable filter frit body that includes a porous hydrophilic polyethylene material. The body could also be formed using a membrane or other filter materials, and does not necessarily have to be form-stable. The integrated gel filtration frit can have a length dimension, a width dimension, and a depth dimension, wherein each of the dimensions is less than 50 mm.

According to various embodiments, a microfluidic device is provided having a channel formed in a substrate and an integrated gel filtration frit disposed in the channel, for example, as shown in FIG. 6. According to various embodiments, a microfluidic device can be provided having a channel formed in a substrate, an input opening formed in the substrate, an output opening formed in the substrate, a filtration column or chamber formed in the substrate between and in fluid communication with the input opening and the output opening, and an integrated gel filtration frit as described herein disposed in the column, wherein the input opening of the channel is in fluid communication with the opening of the integrated gel filtration frit.

FIGS. 12-16 depict various microfluidic devices 200, each of which is designed with one or more features for restricting the flow of a filtration material through the device. In FIGS. 12 and 14-16, the features are formed in a substrate 220. In the device of FIG. 13, the channels can be formed in an insertable component that can be incorporated into a microfluidic device. In each device, a first channel 208 is in fluid communication with a second channel 210. A fluid communication 212 in the form of a region is provided in each device between the first channel 208 and the second channel 210. In FIGS. 12 and 14-16, the fluid communications 212 are also formed in the substrate 220. Each of FIGS. 12-16 shows flow-restricting material 202 disposed in the first channel 208 and/or the fluid communication 212. As shown in FIGS. 12 and 13, a second material 204 of smaller average diametrical particle cross-section area than material 202 is provided in first channel 208. In FIG. 13, a third material 206 having an even smaller average diametrical particulate cross-sectional area is provided in first channel 208. Each of the materials 202, 204, and 206 can include a gel filtration material, such as, an ion-exchange gel filtration material. Each of the materials 202, 204, and 206 can be an inert material having an average diametrical particle cross-sectional area as described herein, for example, glass or silicon seeds. The microfluidic device 200 can also have baffles 214 as depicted in FIGS. 14 and 15, to further restrict the flow of the flow-restricting material 202 into the second channel 210. The baffles 214 can be provided in the fluid communication 212, in the second channel 210, or in both the fluid communication 212 and in the second channel 210.

Some of the particles of materials 202, 204, and 206 can flow into the second channel 210 before a pile-up of the materials 202, 204, and 206 forms at fluid communication 212. The forming of the pile-up and/or the breakdown of the pile-up at the fluid communication 212 can be manipulated by controlling how much force is applied to the microfluidic device, for example, a centripetal force, or a pneumatic force. The fluid communication 212 can be a tapered transition region, for example, a funnel-shaped transition region. The fluid communication 212 can be a conically-shaped transition region as depicted in FIGS. 12-15.

According to various embodiments, a method to form a microfluidic device 200 as depicted in any one of FIGS. 12-15 is provided. Particulate flow-restricting material 202 is disposed in a first channel 208 having a first cross-sectional area. The first channel 208 terminates at a fluid communication 212 in the form of a region. The particles of the first material 202 can have an average diametrical particle cross-sectional area that is from 5% to about 90% of the diametrical cross-sectional area of the second channel 210. According to various embodiments, an additional material 204 made-up of particles having a smaller cross-sectional area than the first material particles can then be added to the pile-up of the first material particles 202. A third type of material 206 can be added after particulate material 204, the third material 206 can be another flow-restricting particulate material, can be of the same composition but of smaller size than either particulate material 202 or 204, or can be a gel or resin material that can be non-particulate. Diluent initially accompanying or used to load the first and/or second material can be removed from the first channel 208 through the fluid communication 212 and into the second channel 210, for example, by using centripetal force. The diluent can further be removed from the second channel 210 and, for example, removed from the device or stored in a collection or output chamber.

According to various embodiments, the particulate materials 202, 204, and 206 can be gel filtration particles or other particles. The particles can be chemically derivitized or physically modified to provide functions other than restricting flow of subsequently loaded gel or resin materials. For example, the materials 202, 204, and 206 can be modified to allow hybridization with DNA or DNA fragments. In cases where any of materials 202, 204, or 206 are modified to allow hybridization, methods can be provided whereby hybridized components can subsequently be released from the materials, for example, by denaturing. As such, various embodiments can provide a purification or concentration of hybridizable components.

Because the microfluidic devices 200 shown in FIGS. 12-16 can be assembled in place, methods of making the devices can avoid access and handling problems associated with using filtration frits known in the art. For example, the devices 200 can be made smaller than devices incorporating frits known in the art.

According to various embodiments, microfluidic devices such as those shown in FIGS. 12-16 can be provided wherein the direction of the flow of a fluid through the first channel is aligned with the direction of flow of fluid through the second channel. According to various embodiments, microfluidic devices can be provided wherein at least one of the first channel and second channel can include a cross-sectional area orthogonal to the direction of fluid flow, that has a round shape, for example, a circular cross-section.

According to various embodiments, for example, the embodiments shown in FIGS. 12-16, a microfluidic device can be provided that includes a substrate having a first surface, a second surface opposing the first surface, and a thickness. The substrate includes a first channel formed therein that extends in a first direction and that has a first cross-sectional area defined by at least a first minimum dimension and first depth, the first depth extending in the direction normal to the first surface and toward the second surface. The substrate also includes a second channel formed therein and extending in a second direction, wherein the second channel has a second cross-sectional area defined by at least a second minimum dimension and a second depth. The second depth extends in a direction normal to the first surface and toward the second surface. The device further includes a fluid communication formed in the substrate between the first channel and the second channel, and having a third cross-sectional area defined by at least a third minimum dimension, wherein the third cross-sectional area is less than the first cross-sectional area. The device further includes a particulate flow-restricting material disposed in the first channel and comprising flow-restricting particles, wherein at least 10% by weight of the flow-restricting particles includes flow-restricting particles having a particle diameter that is less than the third minimum dimension. According to various embodiments, the first direction and the second direction can be aligned with one another at the fluid communication. According to various embodiments, at least one of the first channel and the second channel includes a cross-section that has a round shape. According to various embodiments, at least 50% by weight of the flow-restricting particles includes flow-restricting particles having a particle diameter that is less than the third minimum dimension. For example, at least 95% by weight of the flow-restricting particles includes flow-restricting particles having a particle diameter that is less than the third minimum dimension. According to various embodiments, the flow-restricting particles have particle diameters that are less than the second minimum dimension. According to various embodiments, the flow-restricting material can include a gel filtration material disposed in the first channel and having an average diametrical cross-sectional area that is less than the third cross-sectional area. The average diametrical cross-sectional area of the flow-restricting particles can be from about 0.1 to about 0.2 times the third cross-sectional area. According to various embodiments, the flow-restricting particles can form a pile-up at the fluid communication. The flow-restricting material can include a first flow-restricting material having particles of a first average diameter packed-together at the fluid communication, and a second flow-restricting material having particles of a second average diameter packed-together in the first channel and adjacent the packed-together first flow-restricting material, and wherein the average diameter of the first flow-restricting material particles is greater than the average diameter of the second flow-restricting material particles. Further, the second packed-together flow-restricting material can be spaced further from the second channel than the packed-together first flow-restricting material.

As shown in FIGS. 16 and 17, microfluidic devices can be provided that include a fluid communication 212 between a first channel 208 and a second channel 210, in the form of an abrupt change in cross-sectional areas.

As exemplified in FIGS. 16 and 17, according to various embodiments, it may be desirable to throttle the flow of fluid or particulate material through the device, to meter the distribution of reagents, and/or to block the flow of particulate material in a microfluidic device. Under such circumstances, it can be useful to employ a flow restrictor according to various embodiments. According to various embodiments, a channel with a cross-sectional area that is significantly smaller than a connecting channel can be used to form a flow restrictor. Depending upon the desired results and restriction, the dimensions of the restriction can be selected, for example, to retain smaller particles in the larger cross-sectional area connecting channel. FIG. 17 shows representative geometries of flow restriction designs that can be used.

According to various embodiments, one or more flow restrictor can be used to prevent the flow of gel filtration particles and/or size-exclusion media into a connecting channel, processing chamber, or output well. The smaller channel can be large enough, however, to allow sample fluids to readily pass through. For example, according to various embodiments, a first channel can include an output end having a first cross-sectional area, and which intersects a second channel having a second cross-sectional area that is from about 5% to about 50% the cross-sectional area of first channel. The cross-sectional area of the second channel can be, for example, from about 6% to about 30% of the cross-sectional area of the first channel, for example, from about 10% to about 15% of the cross-sectional area of the first channel. In an exemplary embodiment, a first channel has a square cross-section with a width of about 0.50 mm and a depth of about 0.50 mm. A second channel in fluid communication with the first channel can be provided with a square cross-section having a width of about 0.18 mm and a depth of 0.18 mm. In such a flow restrictor design, the cross-sectional area of the second channel is about 13% of the cross-sectional area of the first channel. Such a flow restrictor design can be useful in restricting the passage of gel filtration particles that have a minimum dimension of about 0.001 mm or greater, for example, about 0.01 mm or greater, and can be useful in causing a pile-up of gel filtration particles at the transition between the two channels, wherein the gel filtration particles have average cross-sectional areas that are smaller than the cross-sectional area of the second channel, as depicted in FIG. 16.

In such devices, a shoulder is provided at the intersection of the first channel 208 and second channel 210, and the shoulder can be perpendicular to the direction of flow of fluid through the first and second channels.

According to various embodiments, a flow restrictor second channel, such as second channel 210 in FIGS. 12-17, can be formed by opening a valve, to form a fluid communication between two or more first channels or chambers, and a second channel. The dimensions of the intersection or transition between the second channel and one or more first channels defines a flow restrictor as described herein. The fluid communication can be useful for causing a pile-up of gel-filtration at the fluid communication formed by the opening of a valve. Such valves and said valving techniques can include those described in concurrently filed U.S. patent application Ser. No. 10/336,274, now U.S. Pat. No. 7,198,759 B2, which is herein incorporated in its entirety be reference.

FIG. 18 illustrates a manufacturing process for forming a microfluidic device, for example, the device of FIGS. 1 and 2. In a first step, a substrate is formed that includes an input, an output, first and second channels, and a filtration fit column. In a second step, a filtration frit is positioned within the filtration frit column. Positioning can be accomplished by press-fitting the filtration frit into the column, or depending upon tolerances, the filtration frit can simply be dropped into the column. In a third step, the bottom surface of the device is sealed with a cover, for example, by applying a pressure-sensitive adhesive tape to the bottom surface of the substrate.

In a fourth step of the method, the top of the filtration frit column is sealed and half of the input and output openings are sealed.

FIG. 19 depicts a method of fabricating a microfluidic device, such as the device of FIGS. 1 and 2. In a first step, a gel slurry including flow-restricting particles can be filled in a first channel of a device through an input opening. A force can be applied to the device to pack the gel slurry by using, for example, a vacuum at an output opening of the device, or by applying centripetal force to the device. The force can move the gel slurry from the input opening into the first channel. The input opening can be completely sealed after loading the gel slurry by applying a cover, or sealing can be affected after the first channel is packed. After the first channel has been packed, the gel slurry can be dewatered and a cover can be applied to seal the output opening. Thereafter, the device can receive a sample for processing. Force can then be applied to the microfluidic device to manipulate the sample to move from the input opening to the output opening.

According to various embodiments, flow-restricting material, gel filtration material, and sample can all be introduced through the input opening of the device. At any of various times during the process, the input opening can be completely sealed on a first surface of the device with a cover, for example, an optically transparent adhesive cover. The input opening can also be completely or partially sealed on an opposing second surface of the device. This allows for the containment of small samples, for example, samples sizes of from about one nanoliter to about 10 µL, for example, from about 100 nanoliters to about 0.5 µl, that can be pipetted into the input opening.

The various devices and methods described above can be implemented in devices and methods for high-throughput processing of a plurality of samples simultaneously. An example of such a high-throughput device is shown in FIG. 20. FIG. 20 is a top view of a microfluidic device 400 having a plurality of pathways 300, each for processing a respective sample according to various embodiments. The plurality of pathways 300 can be parallel to each other. Each pathway 300 can have an input opening 372 in interruptable and/or openable fluid communication with a plurality of respective processing chambers 376, 378, 381, 383, and 385. Each pathway 300 can terminate at a respective output opening 387, 389, as shown.

In the device of FIG. 20, each pathway 300 can include, in addition to the processing chambers 376, 378, 381, 383, and 385, valves 391, 393, and 397. In various embodiments, each pathway can also include a flow splitter 395 that can divide each pathway 300 into two respective sub-pathways, such as a reverse sequencing reaction pathway and a forward sequencing reaction pathway, with each sub-pathway leading to a separate output chamber or reservoir 387, 389, respectively.

Figure 21:
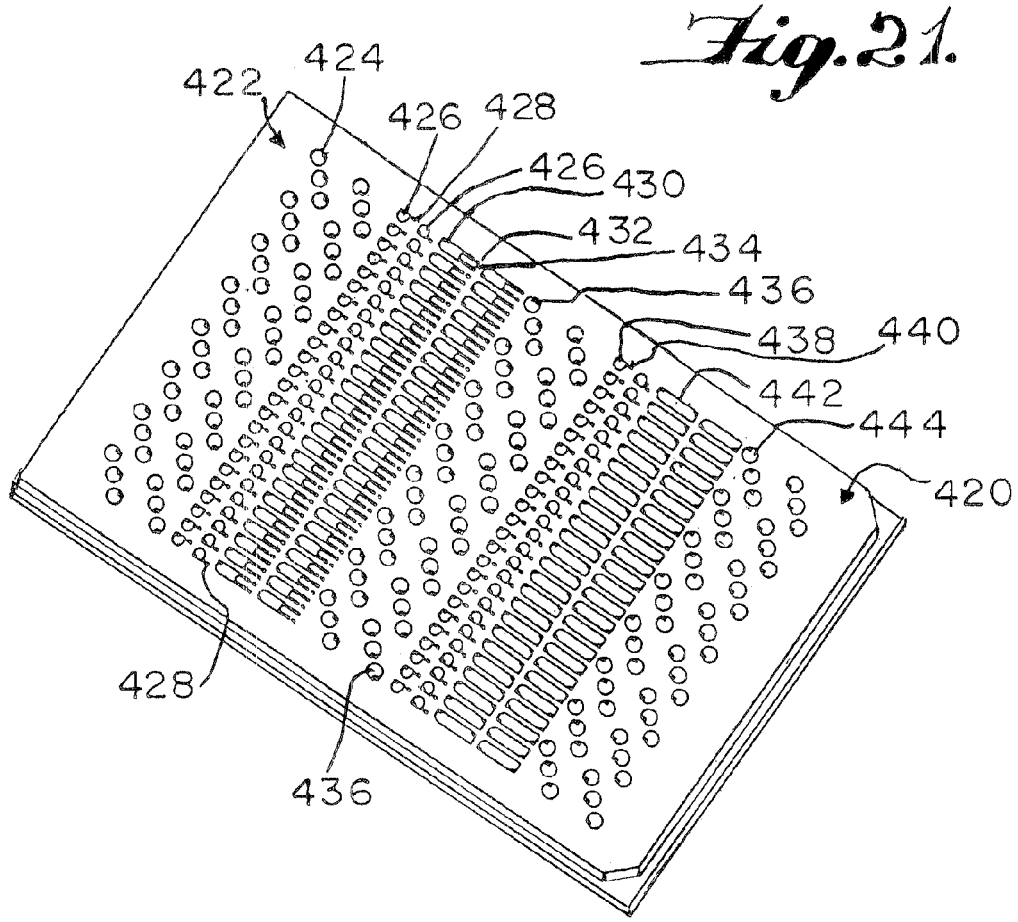
FIG. 21 is a perspective view of an embodiment of a substrate having a plurality of pathways.

FIG. 21 is a top view of another embodiment of a microfluidic device according to various embodiments and having a plurality of pathways 422. According to the exemplary embodiment shown in FIG. 21, each pathway 472 can respectively include an input well 424, a PCR chamber 426, a PCR chamber valve 428, a PCR purification chamber 430, a PCR purification chamber valve 432, a PCR purification chamber appendix 434, a further reaction input well 436, a sequencing chamber 438, a sequencing chamber valve 440, a sequencing purification chamber 442, and an output well, chamber, or reservoir 444, all formed in a substrate 420. Exemplary valves that can be useful in this and other various embodiments include the valves described in U.S. Provisional Patent Application No. 60/398,851 to Bryning et al., which is incorporated herein in its entirety by reference.

Figure 22:
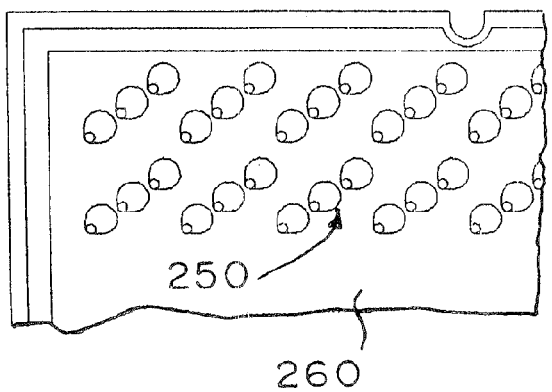
FIG. 22 is a top view of an embodiment that includes a plurality of teardrop-shaped chambers arranged on a cant and formed in a substrate.
Figure 23:
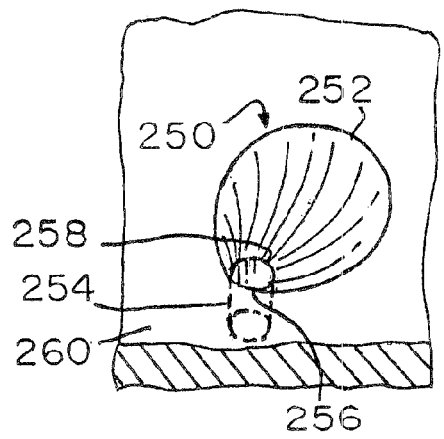
FIG. 23 is an enlarged perspective view of an embodiment of a teardrop-shaped input chamber having a tapering cross-section.

FIGS. 22 and 23 are enlarged views of the input chamber of a device, such as the devices shown in FIG. 21, and show a plurality of teardrop-shaped chambers 250 formed in a substrate 260. The teardrop-shaped chamber 250 can each have a substantially circular first end 252, a narrower and opposite second end 256, and an opening 258 in fluid communication with a channel 254 that leads to a subsequent feature, such as a processing chamber, of the device.

According to various embodiments, teardrop-shaped chamber 250 can have a constant cross-sectional area along the depth of the chamber. According to various embodiments, the bottom of the teardrop-shaped chamber can be scalloped, or it can be flat.

Because the centripetal force exerted on retilinear devices is not necessarily aligned with each pathway, channel, well, or chamber of such devices, a dead volume zone can be created in corners of such. According to various embodiments, to facilitate the complete transfer of samples and prevent portions of sample from being retained, the teardrop-shaped chamber 256 can be employed to direct the sample into the connecting channel 254. This design can be used for all non-radial wells, both to the left or to the right of the center of the device. FIG. 22 depicts an exemplary pattern of such wells.

According to various embodiments, the teardrop-shaped chambers can be canted or rotated 45° with respect to the direction of sample flow through the pathways, to improve the transfer of the samples into and through the pathways. The direction of the cant can depend on the location of the wells with respect to the axis of rotation of the device or of a spinning platen on which the device is held, mounted, affixed, or secured.

According to various embodiments, methods are provided to manipulate a liquid sample in a microfluidic device having a teardrop-shaped chamber and a liquid sample disposed in the chamber. The device can be spun around an axis of rotation that does not lie on any portion of the device. The spinning can centripetally force the liquid sample from the chamber into a channel. Methods are also provided for centripetally manipulating a liquid sample in a channel into a chamber.

Figure 25:
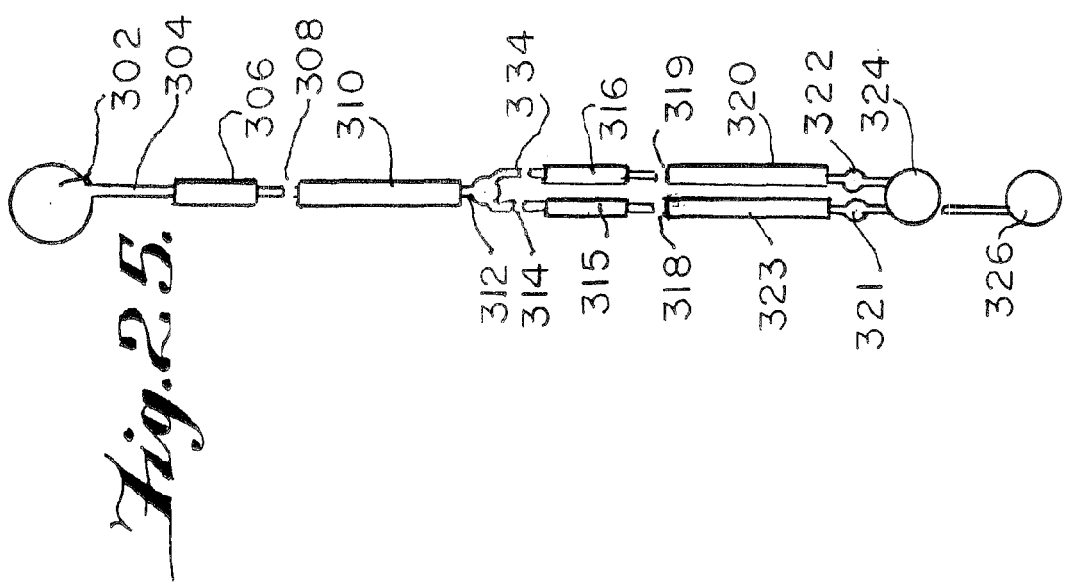
FIG. 25 is an enlarged perspective view of the pathway shown in the device of FIG. 24.
Figure 24:
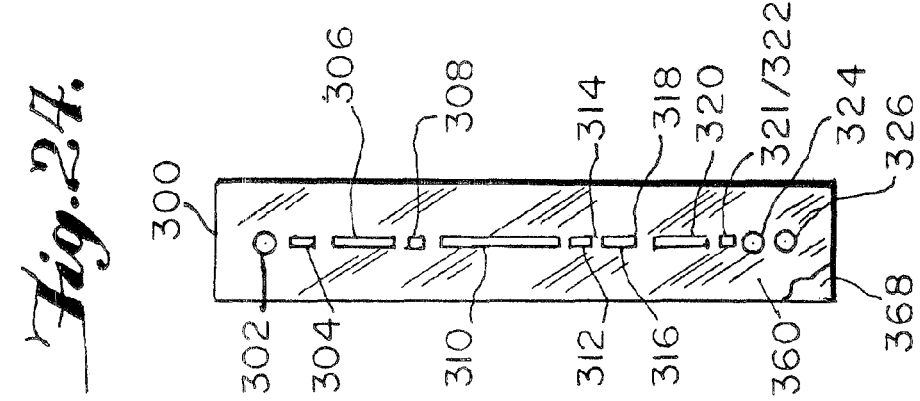
FIG. 24 is a top view of a microfluidic device according to an embodiment having a pathway for processing a sample.

FIG. 24 is a top view of a microfluidic device having a pathway 300 for processing a sample according to various embodiments. FIG. 25 is an enlarged top view of the pathway 300 shown in FIG. 24. The pathway 300 is exemplary of the pathways 300 shown in FIG. 20. The pathway 300 can include an input chamber 302, an input channel 304, a PCR chamber 306, a PCR chamber valve 308, a PCR purification column 310, a PCR purification column valve 312, a flow splitter 334, a flow splitter valve 314, a forward sequencing reaction chamber 315, a reverse sequencing reaction chamber 316, sequencing reaction chamber valves 318, 319, a forward sequencing reaction purification column 323, a reverse sequencing reaction purification column 320, a forward sequencing reaction column valve 321, a reverse sequencing reaction column valve 322, a forward sequencing reaction product output chamber 326, and a reverse sequencing reaction product output chamber 324. The device depicted in FIG. 24 is shown also including a substrate 368 and a cover 360.

According to various embodiments, the channels, chambers, valves and other components of a microfluidic device with parallel pathways can be spaced, for example, 9 mm, 4.5 mm, 3 mm, 2.25 mm, 1.125 mm, or 0.5625 mm, from one another. The pathways 300 can be parallel, and can be arranged and mounted on a rotating platen so as not to lie on a radius of rotational motion. Further details regarding microfluidic devices having geometrically parallel processing pathways, and systems and apparatus including such devices or for processing such devices, are described in concurrently filed U.S. patent application Ser. No. 10/336,274 now, U.S. Pat. No. 7,198,759 B2, and in concurrently filed U.S. patent application Ser. No. 10/336,330, now U.S. Pat. No. 7,041,258 B2, both of which are herein incorporated in their entireties by reference.

According to various embodiments, the device can be loaded with a pipette. Prior to injecting a sample, the device can be pre-loaded with appropriate reactants, reagents, buffers, or other conventionally known components useful for carrying out desired reactions in the device.

According to various embodiments, the microfluidic device can be a laminated, multi-layer polymeric material device that can conform to an SBS microplate format. The microfluidic device can be about 0.5 mm to about 5 mm thick, for example, from about 2.0 mm to about 3.0 mm thick. In its basic form, the microfluidic device can include a substrate that is laminated on both sides with thin cover films. Within the substrate can be a series of channels, chambers, and/or wells that can be used to manipulate a sample fluid along a prescribed path. Fluid samples can be transferred from channel or chamber to channel or chamber by centripetal force. Centripetal force can be generated by rotating the device about an axis of rotation while mounted on a spinning platen. Thus, sample fluid can be transferred from one end of the device to the other as various reactions are sequentially performed.

The device can be rotated such that the fluid moves through the device under centripetal force even if the entire pathway of the device is sealed.

According to various embodiments, a processed sample resulting from the use of the microfluidic device, can be an aqueous, injection-ready sample that can be used in a capillary electrophoresis analytical instrument, for example.

According to various embodiments, the device can include a purification column that can enable the purification of small volumes, for example, volumes of from about one nanoliter to about 10 µl, for example, from about 100 nanoliter to about 0.5 µl. Various embodiments enable the purification of small sample volumes in a high-throughput, parallel, planar format.

According to various embodiments, a microfluidic device is provided having a rectangular substrate.

According to various embodiments, a microfluidic device is provided with a pathway having a first channel and a first chamber at least partially formed in a substrate, and wherein the substrate includes a plurality of such pathways. Each respective chamber has a depth and a teardrop-shaped cross-sectional area when cross-sectioned perpendicular to the depth. The respective chambers each have substantially circular first end, and a narrower and opposite second end. The second ends of the respective chambers are in fluid communication with the respective channels. According to various embodiments, a microfluidic device as such is provided having a plurality of such pathways arranged parallel to one another.

According to various embodiments, a microfluidic device is provided that includes a plurality of parallel sample processing pathways, and at least one valve along each pathway. The at least one valve can include, a first recess formed in a substrate, a second recess formed in the substrate, and an intermediate wall interposed between the first recess and the second recess, wherein the intermediate wall portion is formed from a deformable material having a first elasticity. The valve can also include an elastically deformable cover layer covering the first and second recesses and having a second elasticity that is greater than the first elasticity, in other words, the cover layer can be more elastic or can rebound faster, than the intermediate wall material. The elastically deformable cover layer can contact the intermediate wall when the intermediate wall is in a non-deformed state, and can be out of contact with the intermediate wall when the intermediate wall is in a deformed state, thereby forming a fluid communication between the first and second recesses. Further details of such valves can be found in U.S. Provisional Application No. 60/398,851 filed. Jul. 26, 2002, and in concurrently filed U.S. patent application Ser. No. 10/336,274, now U.S. Pat. No. 7,198,759 B2, which are both incorporated herein in their entirety by reference.

According to various embodiments, a microfluidic device is provided that includes a plurality of parallel processing pathways and at least one valve along each pathway, where the at least one valve includes a first recess formed in a substrate and including a first recess portion and a second recess portion. The first recess is at least partially defined by opposing wall surface portions. The opposing wall surface portions include a first deformable material having a first elasticity. The first recess portion and the second recess portion are in fluid communication with each other when the first deformable material is in a non-deformed state. The at least one valve also includes an elastically deformable cover layer having a second elasticity that is greater than the first elasticity, in other words, the cover layer can be more elastic or can rebound faster, than the deformable opposing wall surface portion. The cover layer covers at least the first recess portion. The opposing wall surface portion that comprises the first deformable material is deformable to form a barrier wall interposed between the first recess portion and the second recess portion, and to prevent fluid communication between the first recess portion and the second recess portion when the barrier wall is in a deformed state.

According to various embodiments, the substrate of the microfluidic device can include a single layer of material, a coated layer of material, a multi-layered material, or a combination thereof. An exemplary substrate can include a single-layer substrate of a hard plastic material, such as a polycarbonate material. Materials that can be used for the microfluidic device or a component thereof, for example, a substrate, base layer, recess-containing layer, or any combination components, can include polycarbonate, polycarbonate/ABS blends, ABS, polyvinyl chloride, polystyrene, polypropylene oxide, acrylics, polybutylene terephthalate (PBT), polyethylene terephthalate (PET), PBT/PET blends, nylons, blends of nylons, polyalkylene materials, fluoropolymers, cyclo-olefin polymers, or combinations thereof. According to various embodiments, the material of the substrate is a cyclic olefin copolymer, for example, ZEONEX, available from ZEON Corporation, Tokyo, Japan, or TOPAZ, available from Ticona GmbH, Frankfurt, Germany.

The entire substrate can include an inelastically deformable material. According to various embodiments having a valve that includes an intermediate wall, at least the intermediate wall can include an inelastically deformable material. The intermediate wall need not be inelastic, but can be sufficiently non-elastic and deformable to enable the formation of a fluid communication between two recesses that the intermediate wall separates upon deformation of the intermediate wall. According to various embodiments, the substrate can include a material that can withstand thermal cycling at temperatures of between 60° C. and 95° C., as for example, are used in polymerase chain reactions. Furthermore, the substrate material can be sufficiently strong to withstand a force necessary to achieve manipulation of a fluid sample through the microfluidic device, for example, centripetal force necessary to spin and manipulate a sample within and through the device.

The substrate can include one or more base layers in contact with a recess-containing layer. The recess-containing layer can be a layer having holes formed therethrough, and a base layer can contact the recess-containing layer and define bottom walls of the through-holes in the recess-containing layer. The substrate can have the same dimensions as the microfluidic device and can make-up a major portion of the thickness of the microfluidic device.

According to various embodiments, the microfluidic device can be provided with an elastically deformable cover layer that at least covers portions of the recess-containing substrate in areas where a portion of the substrate is to be deformed. For example, the cover layer can cover any number of a plurality of chambers or channels formed in the substrate, or cover all of the chambers and channels formed in the substrate. The cover layer can partially cover one or more chambers, input openings, output openings, columns, or other features formed in or on the substrate. The cover layer can have elastic properties that enable it to be temporarily deformed when a deformer contacts the device and deforms an intermediate wall, for example, an intermediate wall located underneath the cover layer. Once such a deformer is removed from contact with the microfluidic device, the deformable intermediate wall can remain in a deformed state while the cover layer elastically rebounds, for at least an amount of time sufficient to enable fluid transfer between two or more recesses that are fluidly connected by deformation of the intermediate wall. The deformable material of the intermediate wall can be elastic to some extent, or can be inelastic.

The elastically deformable cover layer, and/or the substrate, can be chemically resistant and inert. The elastically deformable cover layer can include a material that can withstand thermal cycling at temperatures of between about 60° C. and about 95° C., for example, are used in polymerase chain reactions. Any suitable elastically deformable film material can be used for the cover layer, for example, elastomeric materials. According to various embodiments, PCR tape materials can be used as or with the elastically deformable cover layer. Polyolefin material films, other polymeric films, copolymeric films, and combinations thereof can be used for the cover layer.

The cover layer can be a semi-rigid plate that bends over its entire width or length or that bends or deforms locally. The cover layer can be from about 10 micrometers (μm) to about 500 μm thick, for example, 50 μm to 100 μm, and can include, an adhesive layer. If used, the adhesive layer can be from about 50 μm to about 100 μm thick. Other materials, features, and aspects of the microfluidic devices, device substrates, device cover layers, and device walls, are described in U.S. Provisional Patent Application No. 60/398,851 to Bryning et al., which is incorporated herein in its entirety by reference.

Figure 26:
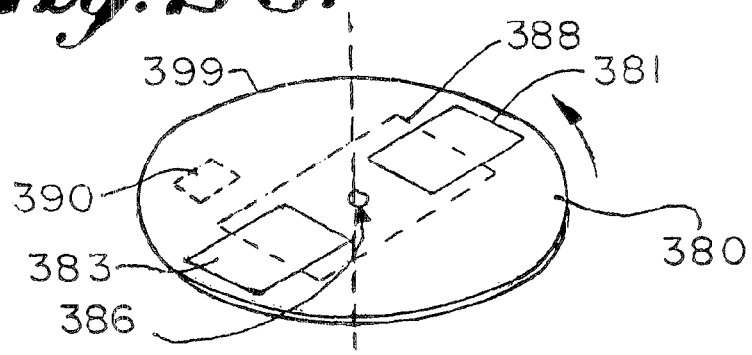
FIG. 26 is a perspective view of an embodiment of a microfluidic system comprising microfluidic devices held on a rotatable platen that can be rotated by a drive unit, heated by a heating element, and controlled by a control unit.

FIG. 26 depicts a microfluidic device processing system 399 that includes a platen 380 that revolves around an axis of rotation 386, holders 381 and 383 for holding and securing the respective microfluidic devices such as the devices shown in FIGS. 20 and 21, a heating element 388, control unit 390. The processing system also includes a drive unit (not shown), and a control unit (not shown) for the drive unit. FIG. 26 shows a direction of rotation with the unmarked arrow, however, the direction of the rotation can be in the opposite direction instead.

Figure 27A:
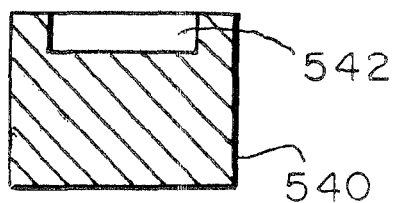
FIGS. 27a-27d are cross-sectional views of a microfluidic channel having various profiles in the substrate.
Figure 27B:
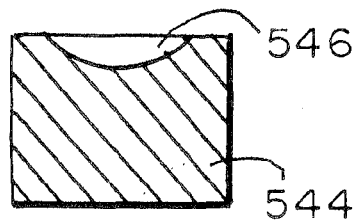
Figure 27C:
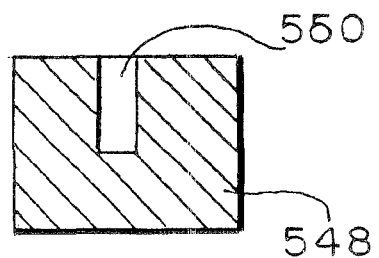
Figure 27D:
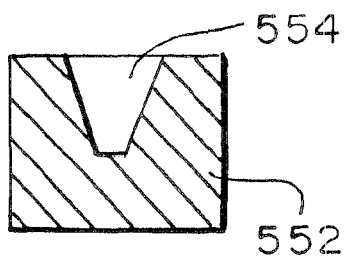

FIGS. 27a-27d are cross-sectional views of various channel profiles that can be used in microfluidic devices according to various embodiments. In FIG. 27a, channel 542 is formed with a rectangular cross-sectional area in a substrate 540. The cross-sectional area can have an aspect ratio, that is a width/depth ratio of greater than one. In FIG. 27b, channel 546 is formed with a semi-oval cross-sectional area in a substrate 544. The cross-sectional area can have an aspect ratio, that is, a width/depth ratio of greater than one. In FIG. 27c, a thin and narrow channel 550 is formed in a substrate 548, wherein the cross-sectional area can have an aspect ratio, that is, a width/depth ratio of less than one. In FIG. 27d, a channel 554 is formed with a trapezoidal cross-sectional area in a substrate 552. These and other cross-sectional designs can be used as flow-restricting channels and can be preformed or formed during a valve-opening operation according to various embodiments.

The dimensional characteristics of a typical, straight channel flow restrictor cross-section can be, for example, about 0.2 mm by about 0.2 mm. The length of such a channel can be, for example, from about 0.1 mm to about 10 cm, for example, about 5 mm. A flow restrictor can be used in conjunction with a larger chamber, greater than approximately 0.50 mm, and serve to retain particles, for example, P-10, SEIE beads, particulates, and SEC beads, located in a chamber. The flow restrictor can be located downstream of the chamber holding the particles. Downstream means the flow restrictor is located at a greater distance from an axis of rotation than the chamber. When subjected to a centripetal force, the materials in the chamber can move toward the flow restrictor where the particulates can be retained while the fluids can pass into an adjacent channel or chamber.

According to various embodiments and as described above, dimensions of the flow restrictor are not limited to square cross-sections. Other shapes can be successfully implemented. For example, a rectangular flow restrictor cross-section having a 0.10 mm depth and a 0.30 mm width can be formed in a substrate to retain gel filtration media such as P-10 beads available from BioRad.

According to various embodiments, the processing system can include microfluidic device holders on the platen that orient parallel pathways of the microfluidic devices off axis with regard to the axis of rotation of the platen. According to various embodiments, a holder can be provided that aligns all of the parallel pathways of a microfluidic device such that when the pathways are parallel to a radius of the platen all of the pathways lie off of the radius and on the same side of the radius.

According to various embodiments, a sample processing system is provided that includes a microfluidic device, having a plurality of parallel pathways disposed in the holder, wherein each input opening of the plurality of pathways is closer to the axis of rotation than each respective output opening of the plurality of pathways. According to various embodiments, each of the plurality of parallel pathways of the device includes a respective input opening, at least one processing chamber, and output opening in a linear arrangement.

According to various embodiments, the microfluidic device used with the sample processing system is shaped as a rectanguloid having a length, a width, and a thickness, and the holder is capable of holding the microfluidic device securely to the platen. Clips, fasteners, or other holding mechanisms can be employed to secure the device to the platen. According to various embodiments, a sample processing system is provided where the microfluidic device has opposing first and second rectangular surfaces, where each of the surfaces has a length that is greater than the width thereof. According to various embodiments, a sample processing system is provided wherein a microfluidic device is disposed in the holder, and a radius of the platen is normal to the length of the microfluidic device and wherein the device includes parallel pathways that extend parallel to the length or the width of the device. According to various embodiments, a sample processing system is provided wherein a microfluidic device is disposed in the holder, and a radius of the platen is normal to the width of the microfluidic device and wherein the device includes parallel pathways that extend parallel to the length or the width of the device.

A description of other materials components and methods useful for various features of the microfluidic devices, systems, and methods described herein, is provided in U.S. Provisional Patent Application No. 60/398,851 to Bryning et al., which is incorporated herein in its entirety by reference.

The foregoing described and other sample processing devices can be processed alone. According to various embodiments, a sample processing device 610 can be mounted on a carrier 680. Such an assembly is depicted in an exploded perspective view of sample processing device 610 and carrier 680 shown in FIG. 28.

By providing a carrier that is separate from the sample processing device, the thermal mass of the sample processing device can be minimally affected as compared to manufacturing the entire sample processing device with a thickness suitable for handling with automated equipment, for example, by robotic arms, and/or processing with conventional equipment. Another potential advantage of a carrier is that the sample processing devices may exhibit a tendency to curl or otherwise deviate from a planar configuration. Attaching the sample processing device to a carrier can retain the sample processing device in a planar configuration for processing. According to various embodiments, the carrier can be made of plastic or other rigid material to provide the carrier with sufficient rigidity when attached to the sample processing device. The plastic carrier can be provided with a rubber pad or rubber pads attached to at least one surface thereof. A silicone foam pad or layer can be used on a surface of the carrier, for example, on the surface that contacts the sample processing device.

The carrier can be provided with limited areas of contact with the sample processing device to which it is mounted, to reduce thermal transmission between the sample processing device and the carrier. The surface of the carrier facing away from the sample processing device can provide limited areas of contact with for example, a platen or other structure used to force the sample processing device against a thermal block to reduce thermal transmission between the carrier and the platen or other structure. The carrier can have a relatively low thermal mass to avoid influencing temperature changes in the sample processing device.

According to various embodiments, the carrier can exhibit some compliance such that the carrier and/or attached sample processing device can conform to the surfaces between which the assembly is compressed, for example, a thermal block and platen. Carriers themselves may not be perfectly planar due to, e.g., variations in manufacturing tolerances, etc. Further, the assemblies may have different thicknesses due to thickness variations in the carrier and/or the sample processing device.

According to various embodiments, the sample processing device 610 can be loaded using centripetal forces. The carrier can maintain the integrity of the sample processing device by applying pressure to the card during loading and/or thermal cycling.

The carrier 680 can be attached to the sample processing device 610 in a manner that allows for the carrier 680 to be reused with many different sample processing devices 610.

According to various embodiments, the carrier 680 can be permanently attached to a single sample processing device 610 such that, after use, both the sample processing device 610 and the carrier 680 are discarded together.

In the depicted embodiment, the sample processing device 610 includes molded posts 611 for aligning the sample processing device 610 to the carrier. At least one of the molded posts can be located proximate a center of the sample processing device 610. Although only one molded post 611 can be used for attaching the sample processing device 610 to the carrier 680, at least two posts 611 can be included. The centrally-located post 611 can assist in centering the sample processing device 610 on the carrier 680, while a second post 611 can be provided to prevent rotation of the sample processing device 610 relative to the carrier 680. Further, although only two posts 611 are depicted, it will be understood that three or more posts or other sites of attachment between the sample processing device 610 and the carrier 680 can be provided. Further, the posts 611 can be melt bonded to the sample processing device 610 to accomplish attachment of the two components in addition to alignment.

Posts or other alignment features can be provided on either or both of the sample processing device 610 and the carrier 680 to generally align the sample processing device 610 with the carrier 680 before the final alignment and attachment using molded posts 611 on the sample processing device 610. The posts and/or other alignment features can align the assembly including the sample processing device 610 and carrier 680 relative to, for example, a thermal processing system used to thermally cycle materials in the sample process chambers 650. One or more alignment features can also be used in connection with a detection system for detecting the presence or absence of a selected analyte in the process chambers 650.

According to various embodiments, posts or other alignment mechanisms can be provided on the carrier 680 to align the carrier 680 with a thermal block. The posts can be arranged as cone-shaped or tapered pins that can mate with corresponding truncated or non-truncated cone-shaped or tapered wells or recesses formed in the thermal block. The posts can be arranged to have a cross-like cross-section, such as a philips head screwdriver tip, that can be compressible and/or elastic, and that can mate with cone-shaped or tapered wells or recesses formed in the thermal block. The posts of the carrier 680 can be made of polypropylene. The wells or recesses formed in the thermal block can have the shape of a truncated cone.

The carrier 680 can include various features such as openings 682 that are preferably aligned with the process chambers 650 of the sample processing device 610. By providing openings 682, the process chambers 650 can be viewed through the carrier 680. One alternative to providing the openings 682 is to manufacture the carrier 680 of a material (or materials) transmissive to electromagnetic radiation in the desired wavelengths. The carrier 680 can be continuous over the surface of the sample processing device 610, that is, the carrier can be provided with no openings formed therethrough for access to the process chambers 650.

Figure 29:
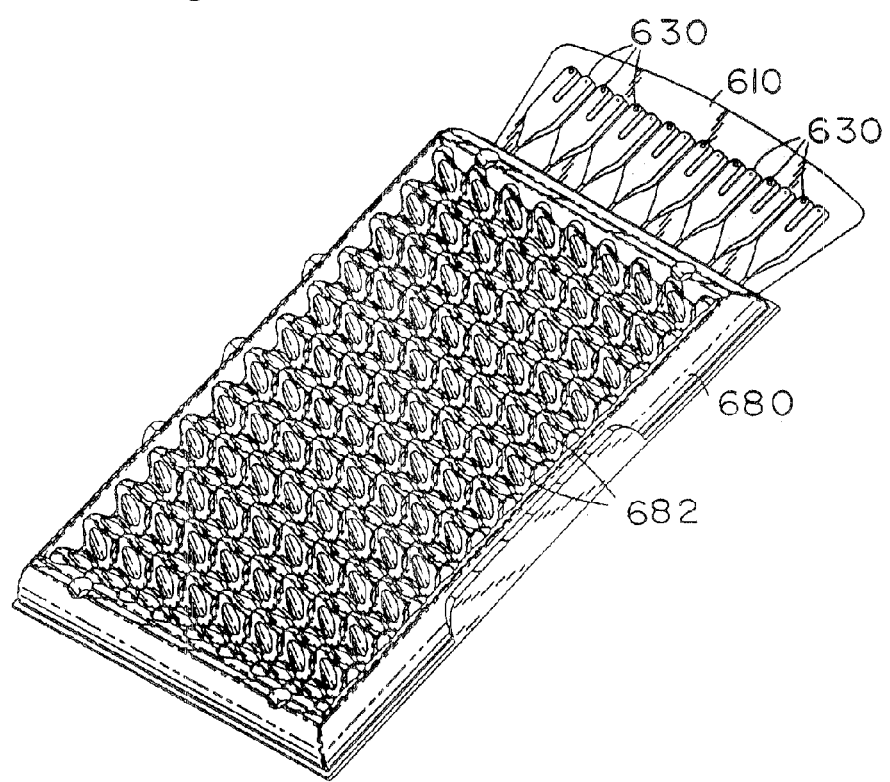
FIG. 29 is a perspective view of the assembly of FIG. 28 as assembled.

The sample processing device 610 and carrier 680 are exemplified in FIG. 29, where it can be seen that the loading chambers 630 can extend beyond the periphery of the carrier 680. As such, the portion of the sample processing device 610 containing the loading structures 630 can be removed from the remainder of the sample processing device 610 after distributing the sample material to the process chambers 650.

Figure 28:
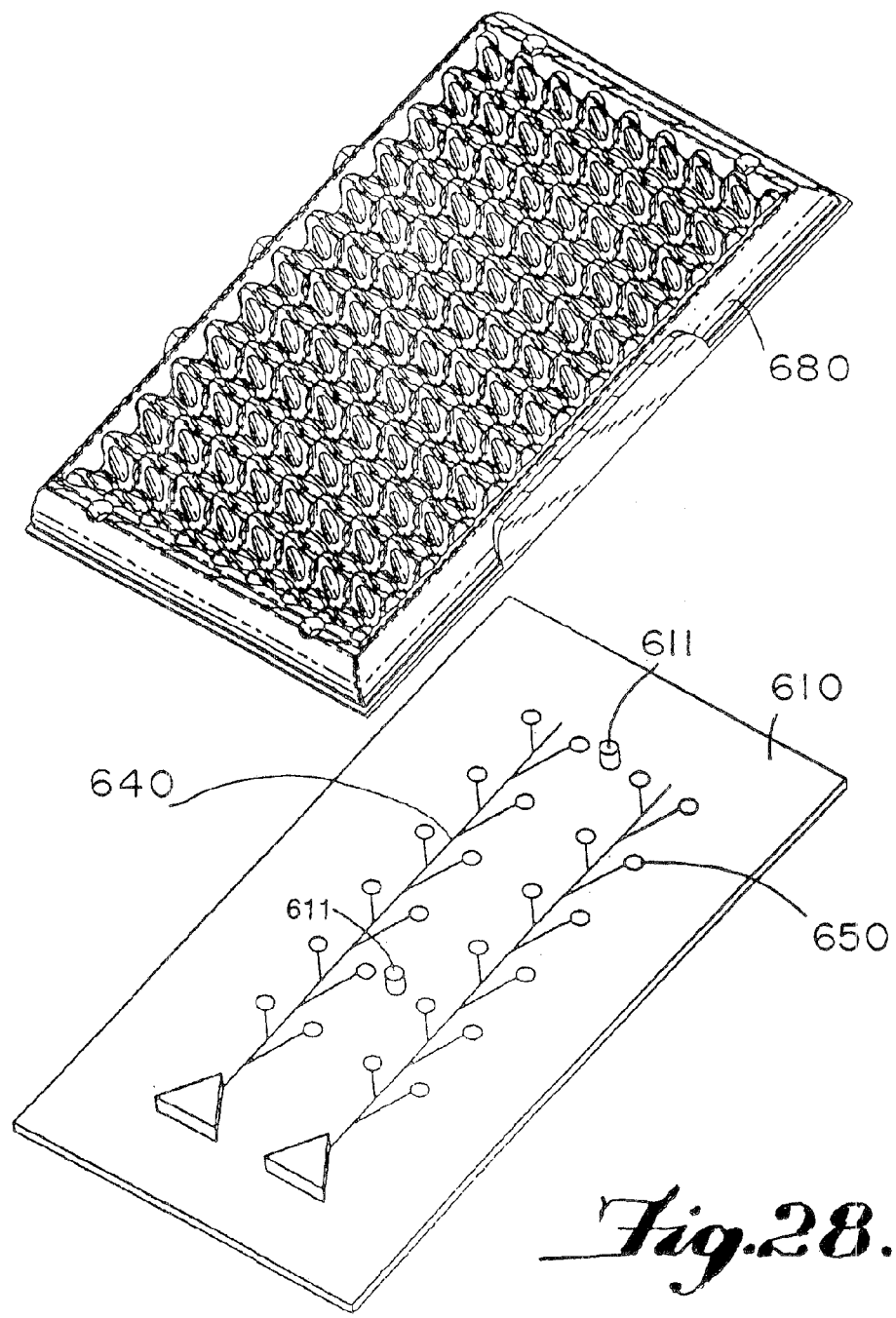
FIG. 28 is an exploded perspective view of an assembly including a sample processing device and a carrier.

The carrier 680 illustrated in FIGS. 28 and 29 can also provide advantages in the sealing or isolation of the process chambers 650 during and/or after loading of sample materials in the process chambers 650.

Figure 30:
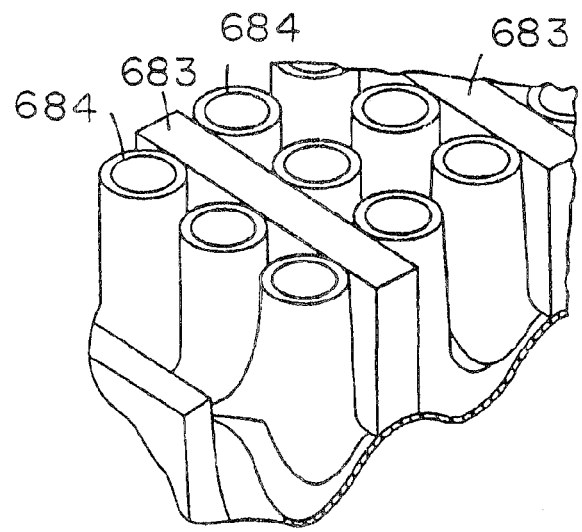
FIG. 30 is an enlarged view of a portion of a carrier depicting one set of main conduit support rails and collars useful in isolating the process chambers on a sample processing device.

FIG. 30 is an enlarged view of a portion of the bottom surface of the carrier 680, that is, the surface of the carrier 680 that faces the sample processing device 610. The bottom surface of the carrier 680 includes a number of features including main conduit support rails 683 that can extend along the length of the main conduits 640 in the associated sample processing device 610. The support rails 683 can, for example, provide a surface against which the main conduits 640 of the sample processing device 610 can be pressed while the conduit 640 is deformed to isolate the process chambers 650 and/or seal the conduits 640 as discussed above.

In addition to their use during deformation of the main conduits 640, the support rails 683 can also be relied on during, e.g., thermal processing to apply pressure to the conduits 640. Furthermore, the use of support rails 683 can also provide an additional advantage in that they provide for significantly reduced contact between the sample processing device 610 and the carrier 680 while still providing the necessary support for sealing of the main conduits 640 on device 610.

Contact between the carrier 680 and device 610 can be reduced or minimized when the assembly is to be used in thermal processing of sample materials, for example as with polymerase chain reactions (PCR). As such, the carrier 680 can be characterized as including a carrier body that is spaced from the sample processing device 610 between the main conduits 640 when the support rails 683 are aligned with the main conduits 640. The voids formed between the carrier body and the sample processing device 610 can be occupied by air or by, for example, a compressible and/or thermally insulating material. According to various embodiments, the carrier 680 can be made from plastic and can have a layer of compressible foam attached to or abutting the surface facing the sample processing device 610, for reducing thermal transmission between the sample processing device 610 and the carrier 680. According to various embodiments, the foam layer can be a silicone foam.

Also depicted in FIG. 28 are a number of optional compression structures 684 which, in the exemplified embodiment, are in the form of collars arranged to align with the process chambers 650 on the sample processing device 610. The collars define one end of each of the openings 682 that extend through the carrier 680 to allow access to the process chambers 650 on sample processing device 610. The compression structures 684, for example, collars, are designed to compress a discrete area of the device proximate each of the process chambers 650 on the sample processing device 610 when the two components (the sample processing device 610 and the carrier 680) are compressed against each other.

That discrete areas of compression can provide advantages such as, for example, improving contact between the device 610 and the thermal block proximate each of the process chambers. That improved contact can enhance the transfer of thermal energy into and/or out of the process chambers. Further, the improvements in thermal transmission can be balanced by only limited thermal transmission into the structure of the carrier 680 itself due, at least in part, to the limited contact area between the sample processing device 610 and the carrier 680.

Another advantage of selectively compressing discrete areas of the device 610 is that weakening of any adhesive bond, delamination of the adhesive, and/or liquid leakage from the process chambers 650 can be reduced or prevented by the discrete areas of compression. This advantage can be particularly advantageous when using compression structures in the form of collars or other shapes that surround at least a portion of the process chambers on the sample processing device.

The collars in the exemplified embodiment are designed to extend only partially about the perimeter of the process chambers 650 and are not designed to occlude the feeder conduit entering the process chamber 650. Alternatively, however, collars could be provided that are designed to occlude the feeder conduits, thereby potentially further enhancing isolation between the process chambers during thermal processing of sample materials.

The collars 684 can optionally provide some reduction in cross-talk between process chambers 650 by providing a barrier to the transmission of electromagnetic energy, for example, infrared to ultraviolet light, between the process chambers 650 during processing and/or analysis of the process chambers 650. For example, the collars 684 can be opaque to electromagnetic radiation of selected wavelengths. Alternatively, the collars 684 can inhibit the transmission of electromagnetic radiation of selected wavelengths by diffusion and/or absorption. For example, the collars 684 can include textured surfaces to enhance scattering, and/or the collars 684 can include materials incorporated into the body of the collar 684 and/or provided in a coating thereon that enhance absorption and/or diffusion.

The carrier 680 can include force transmission structures to enhance the transmission of force from the upper surface of the carrier 680, that is, the surface facing away from the sample processing device, to the compression structures, for example, in the form of collars 684 in the exemplary embodiment, and, ultimately, to the sample processing device itself.

Figure 31:
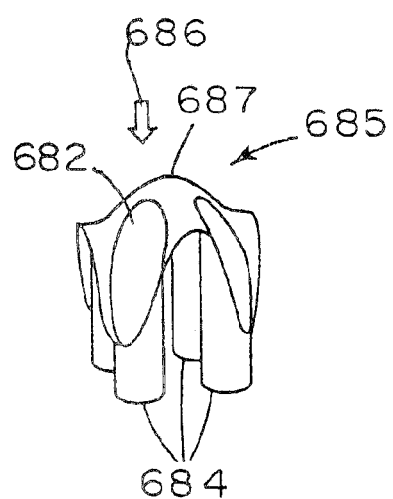
FIG. 31 is a partial cross-sectional view of a portion of a carrier illustrating an example of a force transfer structure useful within the carrier.

FIG. 31 depicts a portion of an illustrative embodiment of a force transmission structure. The force transmission structure is provided in the form of an arch 685 that includes four openings 682 and is operably attached to collars 684. The force transmission structure defines a landing area 687 located between the openings 682 and connected to the collars 684 such that a force 686 applied to the landing area 687 in the direction of the sample processing device is transmitted to each of the collars 684, and, thence, to the sample processing device (not shown). In the depicted embodiment, the landing areas are provided by the crowns of the arches 685.

The arch 685 can transmit the force evenly between the different collars 684 attached to the arch 685, which are essentially provided as hollow columns supporting the arch 685 (by virtue of openings 682). This basic structure is repeated over the entire surface of the carrier 680 as seen in, for example, FIG. 28.

Advantages of providing landing areas on the force transmission structures include the corresponding reduction in contact between the carrier 680 and a platen or other structure used to compress the sample processing device using the carrier 680. That reduced contact can provide for reduced thermal transmission between the carrier 680 and the platen or other structure used to compress the sample processing device. In addition, the force transmission structures and corresponding compression structures on the opposite side of the carrier can all contribute to reducing the amount of material in the carrier 680, thereby reducing the thermal mass of the carrier 680 and, in turn, the assembly of the carrier 680 and a sample processing device.

Figure 32:
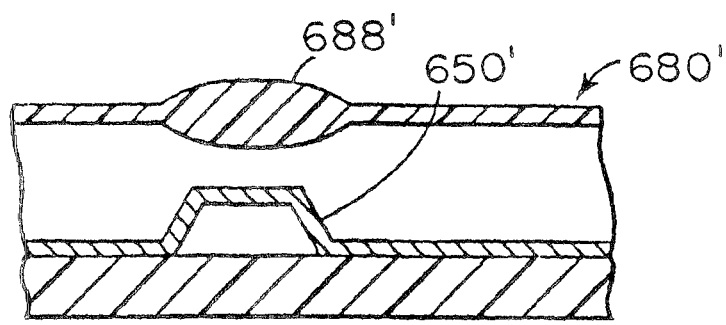
FIG. 32 is a partial cross-sectional view of a carrier and sample processing device assembly including an optical element in the carrier.

FIG. 32 illustrates another optional feature of carriers used in connection with the present invention. The carrier 680' is depicted with an optical element 688', for example, a lens, that can assist in focusing electromagnetic energy directed into the process chamber 650' or emanating from the process chamber 650'. The optical element 688' is depicted as integral with the carrier 680', although it should be understood that the optical element 688' can be provided as a separate article that is attached to the carrier 680'.

Figure 33:
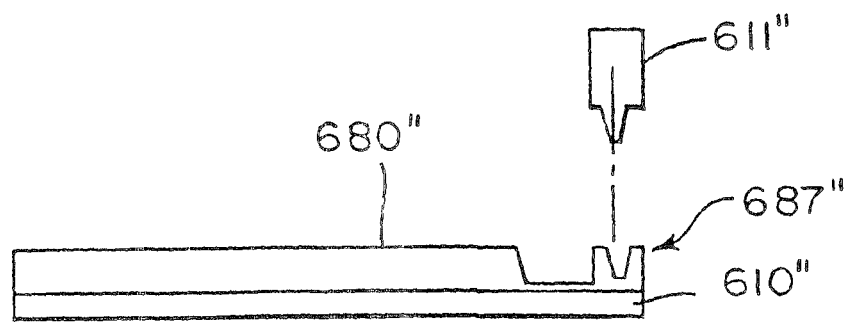
FIG. 33 depicts a carrier and sample processing device assembly including an alignment structure for a sample processing delivery device.

FIG. 33 illustrates yet another optional feature of carriers that can be used. The carrier 680" includes an alignment structure 687" that can be used to assist guiding a pipette 611" or other sample material delivery device into the appropriate loading structure on the sample processing device 610". The alignment structure 687" can be removed with the loading structures on the sample processing device 610" as described herein. The alignment structure 687" can be generally conical as depicted to guide the pipette 611", if it is slightly off-center from an inlet port, into the loading structure on sample processing device 610".

Figure 34:
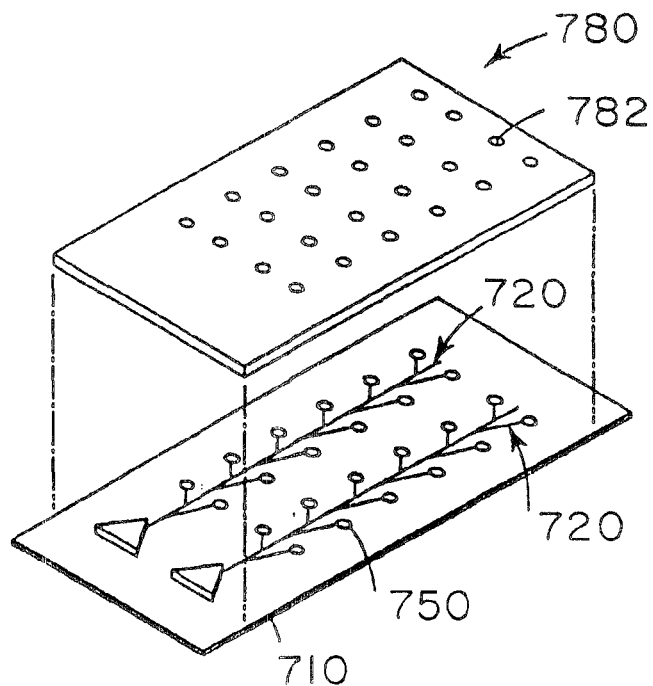
FIG. 34 is an exploded perspective view of another sample processing device and carrier assembly according to various embodiments.

As an alternative the molded carrier depicted in FIGS. 28-31, the carrier can be in the form of a sheet of material in contact with one side of the sample processing device. FIG. 34 is an exploded view of one illustrative sample processing device 710 and a carrier 780 that can be used in connection with the sample processing device 710.

The sample processing device 710 includes a set of process arrays 720, each of which includes process chambers 750 that, in the depicted sample processing device 710, are arranged in an array on the surface of the sample processing device 710. The carrier 780 includes a plurality of openings 782 formed therein that preferably align with the process chambers 750 when the sample processing device 710 and carrier 780 are compressed together.

The carrier 780 can be manufactured of a variety of materials, although it can be preferred that the carrier be manufactured of a compressible material, for example, a sheet of compressible foam or other substance. In addition to compressibility, the compressible material can exhibit low thermal conductivity, low thermal mass, and/or low compression set, particularly at temperatures to which the sample processing device may be subjected. One class of suitable foams can include, for example, silicone based silicone foams.

If the carrier 780 is manufactured from compressible material, there may be no need to provide relief on the surface of the carrier 780 facing the sample processing device 710 to prevent premature occlusion of the conduits in the process arrays 720. If, however, the carrier 780 is manufactured of more rigid materials, it can be desirable to provide some relief in the surface of the carrier 780 for the conduits in the process arrays 720.

Similar to the carrier 680 described above, a carrier 780 such as that depicted in FIG. 34 can provide selective compression of the sample processing device by not compressing the sample processing device in areas occupied by process chambers 750 due to the absence of material located above the process chambers 750. As a result, the carrier 780 can provide several additional advantages. For example, the weakening of the adhesive bond, delamination of the adhesive, and/or liquid leakage from the process chambers 750 can be reduced or prevented by the compression applied to the sample processing device 710 surrounding the process chambers 750. In addition, thermal leakage from, for example, a thermal block against which the assembly can be urged, can be reduced if the material of the carrier 780 is provided with desirable thermal properties, for example, low thermal mass, low thermal conductivity, and the like.

According to various embodiments, openings 782 can provide protection from cross-talk between process chambers 750 by providing a barrier to the transmission of electromagnetic energy, for example, light, between the process chambers 750 during processing and/or analysis of the process chambers 750. For example, the carrier 780 can be opaque and/or non-transmissive of electromagnetic radiation of selected wavelengths. Alternatively, the carrier can inhibit the transmission of electromagnetic radiation of selected wavelengths by diffusion and/or absorption. For example, the openings 782 can include textured surfaces to enhance scattering. Moreover, the carrier 780 can include materials incorporated into the body of the carrier 780, and/or provided in a coating thereon, that can enhance absorption and/or diffusion of selected wavelengths of electromagnetic energy.

According to various embodiments, the carriers described above in connection with FIGS. 28-34 can be fixedly attached to the sample processing device, or the carriers can be separate from the sample processing device. If separate, the carriers can be removably attached to, or brought into contact with, each sample processing device in a manner that facilitates removal from an sample processing device without significant destruction of the carrier. As a result, the carrier can be used with more than one sample processing device. Alternatively, the carrier can be firmly affixed to the sample processing device, such that both components can be discarded after use. In some instances, the carrier can be attached to the system used to process the sample processing device, for example, a platen of a thermocycling system, such that as a sample processing device is loaded for thermal processing, the carrier can be placed into contact with the sample processing device.

Both of the carriers described above are examples of means for selectively compressing together the first side and the second side of a sample processing device, about each process chamber. The compression can occur simultaneously about each process chamber. Many other equivalent structures that accomplish the function of selectively compressing the first side and second side of a sample processing device together about each process chamber can be envisioned by those of skill in the art. In some configurations, the means for selectively compressing, for example, the resilient carrier 780, can apply compressive force over substantially all of the sample processing device outside of the process chambers. In other embodiments, the means for selectively compressing can apply compressive forces in only a localized area about each of the process chambers in the sample processing device, for example, carrier 680 with its associated collars.

Figure 35:
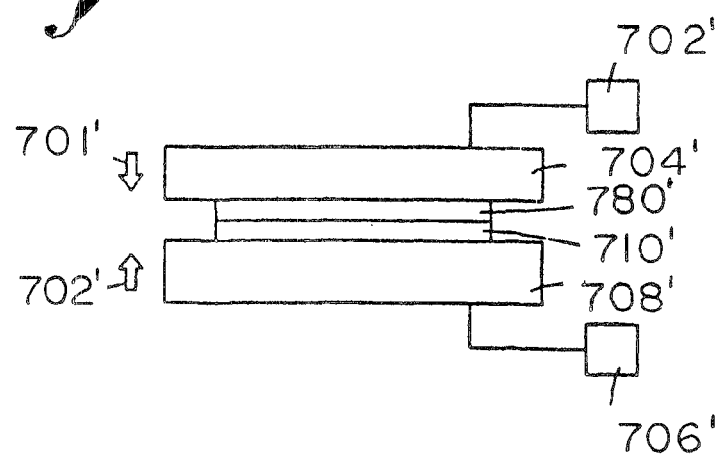
FIG. 35 is a block diagram of a thermal processing system that can be used in connection with sample processing devices.

Any system incorporating a means for selectively compressing can be used to attach the means for selectively compressing to the sample processing device or to a platen or other structure that is brought into contact with the sample processing device during processing. FIG. 35 depicts one thermal processing system that can be used in connection with the sample processing devices in a block diagram format. The system includes a sample processing device 710' located on a thermal block 708'. The temperature of the thermal block 708' is preferably controlled by a thermal controller 706'. On the opposite side of the sample processing device 710', the means for selectively compressing, in the form of carrier 780', is located between the sample processing device 710' and a platen 704'. The platen 704' can be thermally controlled, if desired, by a thermal controller 702' that can, in some instances, be the same as controller 706' controlling the temperature of the thermal block 708'. The sample processing device 710' and the means for selectively compressing 780' can be compressed between the platen 704' and thermal block 708' as indicated by arrows 701' and 702' during thermal processing of the sample processing device 710'.

Those skilled in the art can appreciate from the foregoing description that the broad teachings herein can be implemented in a variety of forms. Therefore, while the devices, systems, and methods herein have been described in connection with particular embodiments and examples thereof, the true scope of the present invention should not be so limited. Various changes and modifications may be made without departing from the scope of the present invention, as defined by the appended claims.

What is claimed is:

1. A sample processing assembly comprising:
a sample processing device comprising:
 a body that comprises a first side attached to a second side, and
 a plurality of process arrays formed between the first and second sides, wherein each process array of the plurality of process arrays comprises a loading structure, a main conduit comprising a length, a plurality of process chambers distributed along the main conduit wherein at least one of the plurality of process chambers includes a filtration material provided in a frit material, and a deformable seal located between the loading structure and the plurality of process chambers, wherein the main conduit is in fluid communication with the loading structure and the plurality of process chambers; and
a carrier attached to the sample processing device, the carrier comprising:
 a first surface facing the sample processing device and a second surface facing away from the sample processing device;
 a plurality of main conduit support rails proximate the first surface of the carrier, wherein each main conduit of the plurality of process arrays is aligned with one main conduit support rail of the plurality of main conduit support rails; and
 a plurality of openings formed through the first and second surfaces of the carrier, wherein each opening of the plurality of openings is aligned with one process chamber of the plurality of process chambers.

2. An assembly according to claim 1, wherein the carrier further comprises a plurality of compression structures proximate the first surface of the carrier, each compression structure of the plurality of compression structures proximate one process chamber of the plurality of process chambers.

3. An assembly according to claim 2, wherein the carrier further comprises a plurality of force transmission structures, each force transmission structure of the plurality of force transmission structures comprising a discrete landing area proximate the second surface of the carrier, and each force transmission structure of the plurality of force transmission structures being operatively connected to a plurality of the plurality of compression structures, wherein a force applied to the landing surface of each force transmission structure is transmitted to the plurality of compression structures operatively connected to the force transmission structure.

4. An assembly according to claim 1, wherein the carrier further comprises a plurality of collars proximate the first surface of the carrier, each collar of the plurality of collars aligned with and proximate to one process chamber of the plurality of process chambers.

5. An assembly according to claim 1, further comprising a plurality of collars proximate the first surface of the carrier, wherein each opening of the plurality of openings is aligned with one collar of the plurality of collars, and further wherein each collar of the plurality of collars is aligned with one process chamber of the plurality of process chambers.

* * * * *